(12) United States Patent
Kim et al.

(10) Patent No.: US 8,772,299 B2
(45) Date of Patent: Jul. 8, 2014

(54) PHENYL PIPERAZINE COMPOUNDS, PHARMACEUTICAL COMPOSITION INCLUDING THE SAME AND USE THEREOF

(75) Inventors: Yonggil Kim, Daejeon (KR); Nahmryune Cho, Daejeon (KR); Yunhee Kim, Gyeonggi-do (KR); Joon Heo, Daejeon (KR); Seonmin Dong, Gyeonggi-do (KR); Mi Kyung Ji, Daejeon (KR); Man-Young Cha, Daejeon (KR); Kiho Lee, Daejeon (KR)

(73) Assignee: SK Biopharmaceuticals Co., Ltd., Seoul (KR)

( * ) Notice: Subject to any disclaimer, the term of this patent is extended or adjusted under 35 U.S.C. 154(b) by 687 days.

(21) Appl. No.: 13/015,717

(22) Filed: Jan. 28, 2011

(65) Prior Publication Data

US 2011/0118264 A1 May 19, 2011

Related U.S. Application Data

(60) Division of application No. 12/474,943, filed on May 29, 2009, now Pat. No. 7,985,752, which is a continuation-in-part of application No. 12/128,999, filed on May 29, 2008, now Pat. No. 7,964,605.

(51) Int. Cl.
*A61K 31/496* (2006.01)
*A61K 31/5377* (2006.01)

(52) U.S. Cl.
CPC ............ *A61K 31/496* (2013.01); *A61K 31/5377* (2013.01)
USPC ..................................................... 514/255.03

(58) Field of Classification Search
CPC .......................... A61K 31/496; A61K 31/5377
USPC ..................................................... 514/255.03
See application file for complete search history.

(56) References Cited

U.S. PATENT DOCUMENTS

| | | | |
|---|---|---|---|
| 4,975,445 A | 12/1990 | Caprathe et al. | |
| 5,006,528 A | 4/1991 | Oshiro et al. | |
| 2004/0001492 A1 | 1/2004 | Johnson | |

FOREIGN PATENT DOCUMENTS

| | | | | |
|---|---|---|---|---|
| WO | 9818797 A | 5/1998 | | |
| WO | WO 98/18797 | * | 5/1998 | ........... C07D 471/04 |
| WO | 9842692 A | 10/1998 | | |
| WO | 2004112729 A | 12/2004 | | |
| WO | 2009145591 A | 5/2009 | | |

OTHER PUBLICATIONS

Sukalovic, et al., "Synthesis, Dopamine D2 Receptor Binding Studies and Docking Analysis of 5-[3-(4-arylpiperazin-1-yl)propyl]-1H-benzimidazole, 5-[2-(4-arylpiperazin-1-yl)ethoxy]-1H-benzimidazole and their analogs," European Journal of Medicinal Chemistry 2005, 40: 481-493 (13 pages).
Kowalski, et al., "The Synthesis of Cyclic and Acyclic Long-chain Arylpiperazine Derivatives of Salicylamides as Serotonin Receptor Ligands," Journal of Heterocyclic Chemistry, Jan.-Feb. 2008, 39(1), 209-214 (6 pages).
International Search Report for Application No. PCT/KR2009/002881, Jan. 7, 2010 (2 pages).
United States Restriction Requirement for U.S. Appl. No. 12/128,999, Mar. 30, 2010 (9 pages).
United States Office Action for U.S. Appl. No. 12/128,999, Jun. 8, 2010 (6 pages).
United States Office Action for U.S. Appl. No. 12/128,999, Jul. 2, 2010 (10 pages).
United States Restriction Requirement for U.S. Appl. No. 12/474,943, Sep. 30, 2010 (9 pages).
United States Office Action for U.S. Appl. No. 12/474,943, Sep. 27, 2010 (8 pages).
Notice of Allowability for U.S. Appl. No. 12/474,943, Dec. 23, 2010 (4 pages).
Notice of Allowability for U.S. Appl. No. 12/128,999, Feb. 8, 2011 (3 pages).
Blier et al., Biol. Psychiatry, 53: 193-203 (2003).
Borsini et al., Psychopharmacology (Berl), 163(2): 121-141 (2002) (Abstract).
Brodkin et al., Pharmacol. Biochem. Behav., 73(2): 359-366 (2002) (Abstract).
Broekkamp et al., European Journal of Pharmacology, 126: 223-229 (1986).
Cryan et al., Neurosci. Biobehav. Rev., 29: 571-625 (2005).
Ho et al., Behav. Brain Res., 136(1): 1-12 (2002).
Nicolas et al., European Journal of Pharmacology, 547: 106-115 (2006).
Njung'e et al., Pharmacol. Biochem. Behav., Jan: 38(1): 63-67 (1991) (Abstract).
Steru et al., Psychopharmacology (Berl), 85(3): 367-370 (1985) (Abstract).
Trevor Archer et al., Scandinavian Journal of Psychology, 28(3): 242-249 (1987) (Abstract).
Bielski et al., J. Clin. Psychiatry, 69: 571-577 (2008).
Grof et al., Int. Clin. Psychopharm., 8(3): 167-172 (1993).
Robinson et al., J. Clin. Psychopharmacol., 10(3): 67S-76S (1990).

* cited by examiner

*Primary Examiner* — Erich A Leeser
(74) *Attorney, Agent, or Firm* — Michael Best & Friedrich LLP

(57) ABSTRACT

The present invention relates to novel piperazine derivatives or pharmaceutically acceptable salts thereof, a process for preparing the same, and in particular, a high binding for Serotonin 1A(5-hydroxytryptamine; 5-HT1A) receptor, a pharmaceutical composition for treatment and/or prevention of depression and anxiety including an effective amount of the piperazine compound, and a method of treating depression, anxiety and other conditions related to 5-HT1A receptor in a mammal.

14 Claims, No Drawings

PHENYL PIPERAZINE COMPOUNDS, PHARMACEUTICAL COMPOSITION INCLUDING THE SAME AND USE THEREOF

CROSS-REFERENCE

The present application is a divisional of and claims priority to U.S. patent application Ser. No. 12/474,943, filed May 29, 2009, which is a continuation-in-part of and claims priority to U.S. patent application Ser. No. 12/128,999, filed May 29, 2008, the entire disclosures of which are hereby incorporated herein by reference.

FIELD OF THE INVENTION

The present invention relates to novel piperazine derivatives or pharmaceutically acceptable salts thereof, a process for preparing the same, and in particular, a high binding for Serotonin 1A(5-hydroxytryptamine; 5-HT1A) receptor, a pharmaceutical composition for treatment and/or prevention of depression and anxiety including an effective amount of the piperazine compound, and a method of treating depression, anxiety and other conditions related to 5-HT1A receptor in a mammal.

BACKGROUND OF THE INVENTION

Depression affects approximately 14 million people in the United States and 340 million people worldwide, making it one of the leading causes of disability [Kessler R C. Et al., JAMA, 2003, 289, 3095-3105]. Depression is also associated with high rates of relapse, recurrence, disability, and death [Hirschfield R M., et al., JAMA, 1997, 277, 333-340; Keller M B., J. Psychopharmacol. 1996, 10(suppl 1); 41-44].

The role of serotonin in the treatment of depressive and anxiety disorders is underscored by the therapeutic action of selective 5-HT reuptake inhibitors acting to enhance the degree of activation of various 5-HT receptor subtypes [Blier P. and Ward M., Biol. Psychiatry, 2003, 53, 193-203]. Selective serotonin reuptake inhibitors(SSRIs) have had significant success in treating depression and related disorders and have become among the most prescribed drugs since 1980s. But, the use of SSRIs leads to the indiscriminate activation of all serotonin receptors and it can be understood as undesirable actions of serotonin in undesirable pathways at undesirable receptor subtypes [Stahl S M., 2008, Essential Psychopharmacology (3$^{rd}$ ed.), 531]. Although there are various treatment options for depressive and anxiety disorders, a need still exists for new drugs with improved tolerability and adequate efficacy.

In contrast to the SSRIs, the 5-HT1A agonist or partial agonist acts directly on postsynaptic serotonin receptors to increase serotonergic neurotransmission. And, the 5-HT1A partial agonists, Buspirone and Gepirone[Robinson D S., et al., J. Clin. Psychopharmacol., 1990, 10(3), 67S-76S; Bielski R J., J. Clin. Psychiatry, 2008, 69(4), 571-577], and 5-HT1A agonist, Flexinoxan [Grof P., International Clin. Psychopharmacology, 1993, 8(3), 167-172], have shown efficacy in clinical trials for the treatment of depression. Moreover, because of their unique pharmacological profile, 5-HT1A agonists possess theoretic advantages in the treatment of major depression relative to other classes of antidepressants. In particular, these drugs are not expected to produce weight gain, sedation, or sexual dysfunctions, which are often encountered with some of the antidepressants introduced in the last 10 years [Blier P. and Ward M., Biol. Psychiatry, 2003, 53, 193-203].

Many reports have disclosed that phenyl piperazine compounds are effectively used for controlling depression and anxiety.

For example, U.S. Pat. No. 5,578,596 discloses that the 2-alkoxy-5,6,7,8-tetrahydroquinoxaline derivatives have a strong affinity for serotonin 1A receptor and are useful for preventing and treating serotonergic neuron-related disease.

These compounds are found to be very effective as therapeutical medicines for managing depression and anxiety.

Active research and development efforts have continued to be directed to the application of phenyl piperazine compounds for the treatment of depression and anxiety.

SUMMARY OF THE INVENTION

In one aspect, the invention provides a piperazine compound represented by Formula (I):

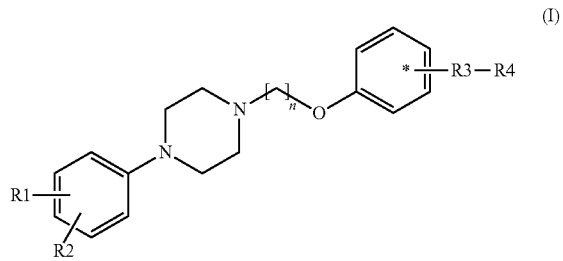

(I)

or pharmaceutically acceptable salts thereof, wherein n is an integer from 2 to 6;

R1 and R2 are the same or different and are independently selected from the group consisting of hydrogen, a hydroxyl group, a halogen, nitrogen dioxide, a straight or branched chain alkyl group with 1 to 4 carbon atoms, and a straight or branched chain alkoxy group with 1 to 4 carbon atoms;

R3 is a C1-C2 alkylene; and

R4 is selected from the group consisting of:
(a) a C2-C6 dialkylamine,
(b) a 5 to 9-membered aromatic amine wherein the ring is independently substituted with at least of hydrogen, a C1-C6 aliphatic alkyl, a C3 to C10 cyclic alkyl, a C6-C10 aryl group and a halogen,
(c) a 5 to 9-membered heteroaromatic amine comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen,
(d) a 5 to 9-membered heterocyclic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen, and
(e) a 5 to 9-membered heteroaromatic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen; and R4 is connected to R3 group through a nitrogen atom therein.

In another aspect, the invention provides a pharmaceutical composition comprising:

(A) an effective amount of a piperazine compound represented by Formula (I):

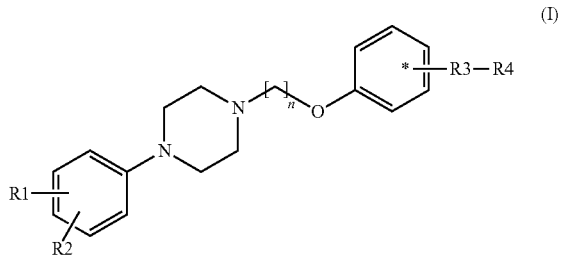

or pharmaceutically acceptable salts thereof, wherein
n is an integer from 2 to 6;

R1 and R2 are the same or different and are independently selected from the group consisting of hydrogen, a hydroxyl group, a halogen, nitrogen dioxide, a straight or branched chain alkyl group with 1 to 4 carbon atoms, and a straight or branched chain alkoxy group with 1 to 4 carbon atoms;

R3 is a C1-C2 alkylene; and

R4 is selected from the group consisting of:
(a) a C2-C6 dialkylamine,
(b) a 5 to 9-membered aromatic amine wherein the ring is independently substituted with at least one of hydrogen, a C1-C6 aliphatic alkyl, a C3 to C10 cyclic alkyl, a C6-C10 aryl group and a halogen,
(c) a 5 to 9-membered heteroaromatic amine comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen,
(d) a 5 to 9-membered heterocyclic ring comprising at least a nitrogen atom as a ring constituent wherein the ring is independently substituted with at least of hydrogen, a C1-C6 aliphatic alkyl, a C3 to C10 cyclic alkyl, a C6-C10 aryl group and a halogen, and
(e) a 5 to 9-membered heteroaromatic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen; and R4 is connected to R3 group through a nitrogen atom therein; and (B) a pharmaceutically acceptable carrier or excipient.

In yet another aspect, the invention provides a method for treating at least one of depression and anxiety in a mammal comprising administering to a mammal in need thereof an effective amount of a piperazine compound represented by Formula (I):

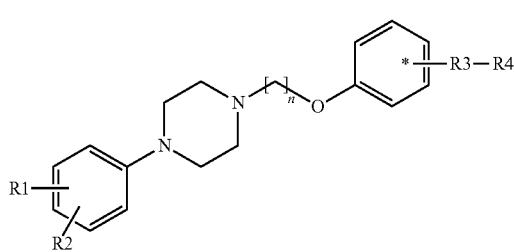

or pharmaceutically acceptable salts thereof, wherein
n is an integer from 2 to 6;

R1 and R2 are the same or different and are independently selected from the group consisting of hydrogen, a hydroxyl group, a halogen, nitrogen dioxide, a straight or branched chain alkyl group with 1 to 4 carbon atoms, and a straight or branched chain alkoxy group with 1 to 4 carbon atoms;

R3 is a C1-C2 alkylene; and

R4 is selected from the group consisting of:
(a) a C2-C6 dialkylamine,
(b) a 5 to 9-membered aromatic amine wherein the ring is independently substituted with at least one of hydrogen, a C1-C6 aliphatic alkyl, a C3 to C10 cyclic alkyl, a C6-C10 aryl group and a halogen,
(c) a 5 to 9-membered heteroaromatic amine comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen,
(d) a 5 to 9-membered heterocyclic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen, and
(e) a 5 to 9-membered heteroaromatic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen; and R4 is connected to R3 group through a nitrogen atom therein.

DETAILED DESCRIPTION OF THE INVENTION

Before any embodiments of the invention are explained in detail, it is to be understood that the invention is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as, for instance, hydrates. Isomers may be separated using conventional techniques, e.g. chromatography or fractional crystallization. The enantiomers may be isolated by separation of racemates for example by fractional crystallization, resolution, or HPLC. The diastereomers may be isolated by separation of isomer mixtures for instance by fractional crystallization, HPLC, or flash chromatography.

A "heteroaromatic ring" or a "heterocylic ring" means a ring containing at least one heteroatom. A "heteroatom" means an atom other than carbon in the ring of a heterocylic group or a heteroaromatic group. Heteroatoms may be at least one of oxygen, sulfur, and nitrogen atoms. Groups containing more than one heteroatom may contain different heteroatoms.

An "effective amount" means any amount that yields a therapeutic effect.

"Pharmaceutically acceptable" means suitable for use in a human or other mammal.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

"Pharmaceutically acceptable carrier" means a carrier that is useful for the preparation of a pharmaceutical composition that is generally compatible with the other ingredients of the composition, not deleterious to the recipient, and neither biologically nor otherwise undesirable. "A pharmaceutically acceptable carrier" includes one or more than one carrier. Embodiments include carriers for parenteral, intravenous, intraperitoneal, intramuscular, sublingual, nasal and oral administration. "Pharmaceutically acceptable carrier" also includes agents for preparation of aqueous dispersions and sterile powders for injection or dispersions.

The piperazine compounds of the invention have Chemical Formula (I) or pharmaceutically acceptable salts thereof.

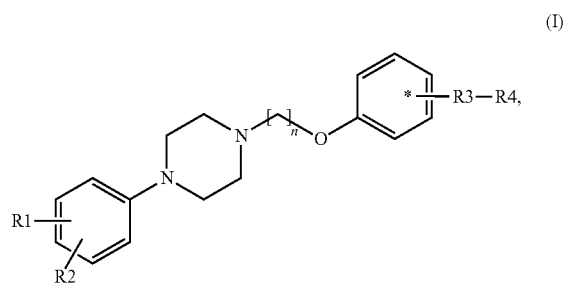

(I)

wherein n is an integer from 2 to 6;

R1 and R2 are the same or different and are independently selected from the group consisting of hydrogen, a hydroxyl group, a halogen, nitrogen dioxide, a straight or branched chain alkyl group with 1 to 4 carbon atoms, and a straight or branched chain alkoxy group with 1 to 4 carbon atoms;

R3 is a C1-C2 alkylene; and

R4 is selected from the group consisting of:

(a) a C2-C6 dialkylamine, (b) a 5 to 9-membered aromatic amine wherein the ring is independently substituted with at least of hydrogen, a C1-C6 aliphatic alkyl, a C3 to C10 cyclic alkyl, a C6-C10 aryl group and a halogen, (c) a 5 to 9-membered heteroaromatic amine comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen, (d) a 5 to 9-membered heterocyclic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen, and (e) a 5 to 9-membered heteroaromatic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen; and R4 is connected to R3 group through a nitrogen atom therein.

In one embodiment, R1 and R2 are independently selected from the group consisting of hydrogen, a hydroxyl group, a halogen, nitrogen dioxide, a straight or branched chain alkyl group with 1 to 4 carbon atoms, and a straight or branched chain alkoxy group with 1 to 4 carbon atoms. For example, the halogen may be F, Cl, Br, or I. The alky group may be methyl, ethyl, n-propyl, isopropyl, n-butyl, iso-butyl, sec-butyl, and t-butyl, and particularly may be methyl, ethyl, propyl, isopropyl, and tertiary butyl. Unless otherwise stated or indicated, the term "alkoxy" denotes a group O-alkyl, wherein alkyl is methyl, ethyl, n-propyl, isopropyl, n-butyl, iso-butyl, sec-butyl, or t-butyl.

Unless otherwise stated or indicated, the term "halogen" shall mean fluorine, chlorine, bromine, or iodine.

Examples of R4 include, without limitation, dimethyl amine, diethylamine, dipropylamine, methylethyl amine, methylpropyl amine, methylbutyl amine, and ethylpropy amine.

When R4 is a 5 to 9-membered aromatic amine or a 5 to 9-membered heteroaromatic amine, R4 is connected to R3 through a nitrogen atom in an amino group.

R4 may be a 5 to 9-membered aromatic amine wherein the ring is independently substituted with at least one of hydrogen, a C1-C6 aliphatic alkyl, a C3 to C10 cyclic alkyl, a C6-C10 aryl group and a halogen. In one embodiment, examples of a 5 to 9-membered aromatic amine in R4 is a 5 or 6-membered aromatic amine substituted with at least one of hydrogen, a C1-C6 alkyl, and a halogen, and particularly, a 6-membered aromatic amine substituted with hydrogen, such as aniline.

R4 may be a 5 to 9-membered heteroaromatic amine containing at least a nitrogen atom where the ring is independently substituted with at least one of hydrogen, a C1-C6 aliphatic alkyl, a C3 to C10 cyclic alkyl, a C6-C10 aryl group, and a halogen. In one embodiment, examples of a 5 to 9-membered heteroaromatic amine include a 5 or 6-membered heteroaromatic amine substituted with at least one of a C1-C6 alkyl and a halogen, wherein the heteroaromatic amine comprises at least two heteroatoms as ring constituents where a first heteroatom is N and a second heteroatom is independently selected from the group consisting of N, O, and S.

The 5-membered heteroaromatic amine may have a structure (II) selected from the group consisting of:

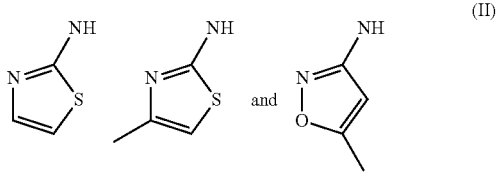

(II)

When R4 is a 5 to 9-membered heterocyclic ring or a 5 to 9-membered heteroaromatic ring, R4 may be connected to R3 through a nitrogen atom contained in the ring as a heteroatom of the 5 to 9-membered heterocyclic ring or heteroaromatic ring.

R4 may be a 5 to 9-membered heterocyclic ring containing at least a nitrogen atom where the ring is independently substituted with at least one of hydrogen, a C1-C6 aliphatic alkyl, a C3 to C10 cyclic alkyl, a C6-C10 aryl group, and a halogen. Examples of a 5 to 9-membered heterocyclic ring include, without limitation, a 5 or 6-membered heterocylic ring having a structure (III) selected from the group consisting of:

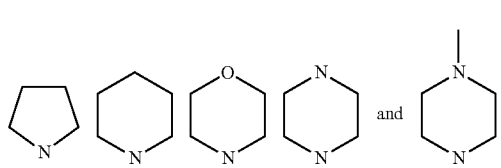

(III)

R4 may be a 5 to 9-membered heteroaromatic ring containing at least a nitrogen atom where the ring is independently substituted with at least one of hydrogen, a C1-C6 aliphatic alkyl, a C3 to C10 cyclic alkyl, a C6-C10 aryl group, and a halogen. Examples of a heteroaromatic ring include, without limitation, an azole compound such as diazole, triazole, tetraazol, benzotriazole, imidazole, pyrazole, benzimidazloe or indazole. The azole ring may be independently substituted with at least one of hydrogen, a C1-C6 aliphatic alkyl, a C3 to C10 cyclic alkyl, a C6-C10 aryl group, and a halogen. The azole compound may have a structure (IV) selected from the group consisting of:

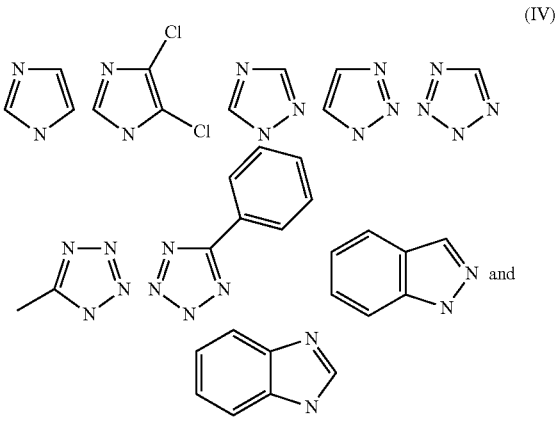

(IV)

Examples of compounds having Chemical Formula (I) include, without limitation, 1-[4-(4-imidazol-1-ylmethyl-phenoxy)-butyl]-4-(2-methoxy-phenyl)-piperazine, 1-(2-methoxy-phenyl)-4-[4-(4-[1,2,4]triazol-1-ylmethyl-phenoxy)-butyl]-piperazine, 1-(2-methoxy-phenyl)-4-[4-(4-tetrazol-1-ylmethyl-phenoxy)-butyl]-piperazine, 1-(2-methoxy-phenyl)-4-[4-(4-tetrazol-2-ylmethyl-phenoxy)-butyl]-piperazine, 1-[4-(3-imidazol-1-ylmethyl-phenoxy)-butyl]-4-(2-methoxy-phenyl)-piperazine-hydrochloride, 1-(2-methoxy-phenyl)-4-[4-(3-[1,2,4]triazol-1-ylmethyl-phenoxy)-butyl]-piperazine hydrochloride, 1-(2-methoxy-phenyl)-4-[4-(3-tetrazol-1-ylmethyl-phenoxy)-butyl]-piperazine hydrochloride, 1-(2-methoxy-phenyl)-4-[4-(3-tetrazol-2-ylmethyl-phenoxy)-butyl]-piperazine hydrochloride, 1-(4-{4-[4-(2-methoxy-phenyl)-piperazin-1-yl]-butoxy}-benzyl)-1H-benzoimidazole, 1-(2-Methoxy-phenyl)-4-{4-[4-(2-methyl-imidazol-1-ylmethyl)-phenoxy]-butyl}-piperazine, 1-(2-methoxy-phenyl)-4-[4-(4-[1,2,3]triazol-2-ylmethyl-phenoxy)-butyl]-piperazine, 1-(2-methoxy-phenyl)-4-[4-(4-[1,2,3]triazol-1-ylmethyl-phenoxy)-butyl]-piperazine, 1-(4-{4-[4-(2-Methoxy-phenyl)-piperazin-1-yl]-butoxy}-benzyl)-1H-indazole, 1-(4-{4-[4-(2-Methoxy-phenyl)-piperazin-1-yl]-butoxy}-benzyl)-1H-benzotriazole, 1-(2-methoxy-phenyl)-4-{4-[4-(5-phenyl-tetrazol-2-ylmethyl)-phenoxy]-butyl}-piperazine, 1-(2-methoxy-phenyl)-4-{4-[4-(5-phenyl-tetrazol-1-ylmethyl)-phenoxy]-butyl}-piperazine, 1-(2-methoxy-phenyl)-4-{4-[4-(5-methyl-tetrazol-2-ylmethyl)-phenoxy]-butyl}-piperazine, 1-(2-methoxy-phenyl)-4-{4-[4-(5-methyl-tetrazol-1-ylmethyl)-phenoxy]-butyl}-piperazine, (4-{4-[4-(2-methoxy-phenyl)-piperazin-1-yl]-butoxy}-benzyl)-dimethyl-amine di-hydrochloride, 1-(2-methoxy-phenyl)-4-[4-(4-piperidin-1-ylmethyl-phenoxy)-butyl]-piperazine, (4-{4-[4-(2-methoxy-phenyl)-piperazin-1-yl]-butoxy}-benzyl)-phenyl-amine, (4-{4-[4-(2-methoxy-phenyl)-piperazin-1-yl]-butoxy}-benzyl)-thiazol-2-yl-amine, 1-(2-chloro-phenyl)-4-[4-(4-[1,2,4]triazol-1-ylmethyl-phenoxy)-butyl]-piperazine, 1-(2-methoxy-phenyl)-4-[4-(3-[1,2,3]triazol-2-ylmethyl-phenoxy)-butyl]-piperazine, 1-(2-Methoxy-phenyl)-4-[4-(3-[1,2,3]triazol-1-ylmethyl-phenoxy)-butyl]-piperazine, 1-(2-Methoxy-phenyl)-4-[4-(3-[1,2,3]triazol-2-ylmethyl-phenoxy)-butyl]-piperazine, 1-(2-methoxy-phenyl)-4-{4-[3-(5-methyl-tetrazol-1-ylmethyl)-phenoxy]-butyl}-piperazine, (3-{4-[4-(2-methoxy-phenyl)-piperazin-1-yl]-butoxy}-benzyl)-dimethyl-amine, 4-(3-{4-[4-(2-methoxy-phenyl)-piperazin-1-yl]-butoxy}-benzyl)-morpholine, 1-{4-[4-(4,5-dichloro-imidazol-1-ylmethyl)-phenoxy]-butyl}-4-(2-methoxy-phenyl)-piperazine, 1-(2-chloro-phenyl)-4-[4-(4-tetrazol-2-ylmethyl-phenoxy)-butyl]-piperazine, 4-(4-{4-[4-(2-methoxy-phenyl)-piperazin-1-yl]-butoxy}-benzyl)-morpholine, (4-{4-[4-(2-Chloro-phenyl)-piperazin-1-yl]-butoxy}-benzyl)-dimethyl-amine, 1-(3-fluoro-phenyl)-4-[4-(4-[1,2,4]triazol-1-ylmethyl-phenoxy)-butyl]-piperazine, 1-(2-methoxy-phenyl)-4-[4-(4-4-methylpiperazine-1-ylmethyl-phenoxy)-butyl]-piperazine, 1-(2,3-dichloro-phenyl)-4-[4-(4-tetrazol-2-ylmethyl-phenoxy)-butyl]-piperazine, 1-(2,3-Dichloro-phenyl)-4-{4-[4-(5-methyl-tetrazol-1-ylmethyl)-phenoxy]-butyl}-piperazine, 1-(2,3-Dichloro-phenyl)-4-{4-[4-(5-methyl-tetrazol-2-ylmethyl)-phenoxy]-butyl}-piperazine, (4-{4-[4-(2,3-dichloro-phenyl)-piperazin-1-yl]-butoxy}-benzyl)-dimethyl-amine, 4-(4-{4-[4-(2,3-Dichloro-phenyl)-piperazin-1-yl]-butoxy}-benzyl)-morpholine, 1-(2-methoxy-phenyl)-4-[4-(4-4-methylpiperazine-1-ylmethyl-phenoxy)-butyl]-piperazine, 1-(2-chloro-phenyl)-4-[4-(4-[1,2,3]triazol-1-ylmethyl-phenoxy)-butyl]-piperazine, (4-{4-[4-(2-Methoxy-phenyl)-piperazin-1-yl]-butoxy}-benzyl)-[1,3,4]thiadiazol-2-yl-amine, 1-(2,3-dichloro-phenyl)-4-[4-(4-[1,2,3]triazol-1-ylmethyl-phenoxy)-butyl]-piperazine, (4-{4-[4-(2-Methoxy-phenyl)-piperazin-1-yl]-butoxy}-benzyl)-(5-methyl-isoxazol-3-yl)-amine, (4-{4-[4-(2-methoxy-phenyl)-piperazin-1-yl]-butoxy}-benzyl)-(5-methyl-isoxazol-3-yl)-amine, 1-{4-[4-(2-imidazol-1-yl-ethyl)-phenoxy]-butyl}-4-(2-methoxy-phenyl)-piperazine, 1-(2-methoxy-phenyl)-4-{4-[4-(2-[1,2,4]triazol-1-yl-ethyl)-phenoxy]-butyl}-piperazine, 1-(2-methoxy-phenyl)-4-{4-[4-(2-[1,2,3]triazol-2-yl-ethyl)-phenoxy]-butyl}-piperazine, 1-(2-methoxy-phenyl)-4-{4-[4-(2-[1,2,3]triazol-1-yl-ethyl)-phenoxy]-butyl}-piperazine, 1-(2-methoxy-phenyl)-4-{4-[4-(2-tetrazol-2-yl-ethyl)-phenoxy]-butyl}-piperazine, 1-(2-methoxy-phenyl)-4-{4-[4-(2-tetrazol-1-yl-ethyl)-phenoxy]-butyl}-piperazine, 1-(2-Methoxy-phenyl)-4-(4-{4-[2-(5-methyl-tetrazol-1-yl)-ethyl]-phenoxy}-butyl)-piperazine, 1-(2-Methoxy-phenyl)-4-(4-{4-[2-(5-methyl-tetrazol-2-yl)-ethyl]-phenoxy}-butyl)-piperazine, 2-{4-[4-(4-[1,2,3]-triazol-1-ylmethyl-phenoxy)-butyl]-piperazin-1-yl}-benzonitrile, and 1-(2-chloro-phenyl)-4-[4-(4-[1,2,3]triazol-2-ylmethyl-phenoxy)-butyl]-piperazine.

A "pharmaceutically acceptable salt", where such salts are possible, includes both pharmaceutically acceptable acid and base addition salts. A suitable pharmaceutically acceptable salt of a compound of Formula I is, for example, an acid-addition salt of a compound of Formula I that is sufficiently basic, for example an acid-addition salt with an inorganic or organic acid such as hydrochloric, hydrobromic, sulphuric, trifluoroacetic, citric or maleic acid; or, for example, a salt of a compound of Formula I that is sufficiently acidic, for example an alkali or alkaline earth metal salt such as a sodium, calcium, or magnesium salt, or an ammonium salt, or a salt with an organic base such as methylamine, dimethylamine, trimethylamine, piperidine, morpholine, or tris-(2-hydroxyethyl)amine.

A method for preparing the above piperazine derivative, represented by chemical Formula (I) will be described below in detail.

First, phenols of Formula (VI) as starting material are reacted with dihalide alkanes represented by Formula (V) to synthesize halogenized compounds represented by Formula (VII):

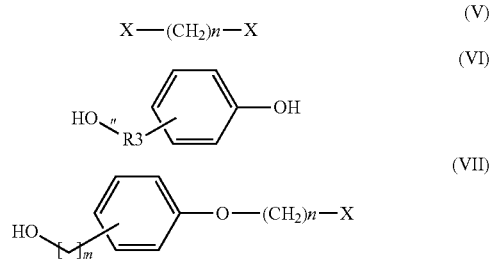

wherein n is the same as defined above and X is a halogen such as, without limitation, chloride and bromide.

The halogenized compound represented by Formula (VII) is reacted with phenyl piperazines of Formula (VIII) to obtain the compounds having hydroxy group represented by the Formula (IX):

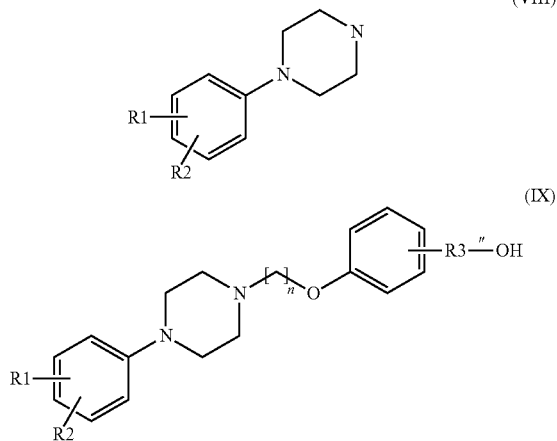

wherein R1, R2, n and R3 are the same as defined above.

This procedure is summarized as set forth in Reaction Scheme (I) below.

Reaction Scheme I

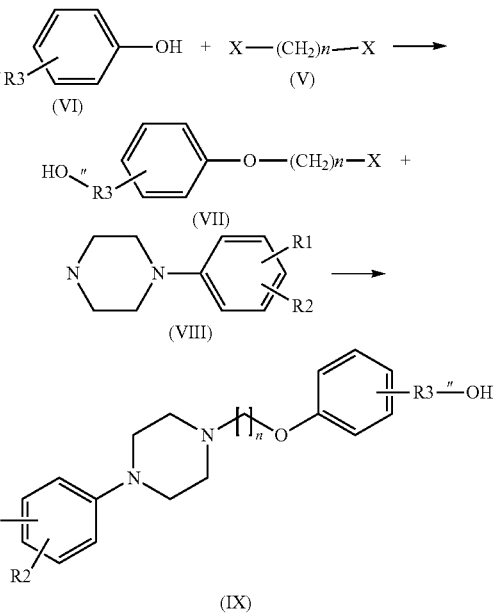

Details of the reaction conditions described in Reaction Scheme I may be as follows. For the conversion of the phenols (VI) to the halogenized compound (VII), the concentration of the phenols (VI) may be about 0.005 to about 0.1 moles, with a dihalide alkane (V) ranging from about 2.0 to about 3.0 equivalents and an organic or inorganic base from about 3.0 to about 4.0 equivalents. This reaction may be refluxed. The resulting product may be purified by column chromatography. For the conversion of the halogenized compounds (VII) to the compound having hydroxy group (IX), a mixture of (VII) and substituted phenylpiperazine (VIII) may be refluxed in about 30 ml of acetonitrile for about 6 h. For this coupling reaction, an ethereal solvent such as diethyl ether and tetrahydrofuran, a halogenated hydrocarbon solvent such as dichloromethane and chloroform, or a mixture thereof may be used.

Then, the hydroxy compounds having hydroxy group represented by Formula (IX) are reacted with thionyl chloride and then with dialkylamines, aromatic amine, heteroaromatic amine, heterocyclic ring, or heteroaromatic ring groups to produce the phenyl piperazine compounds represented by Formula (I):

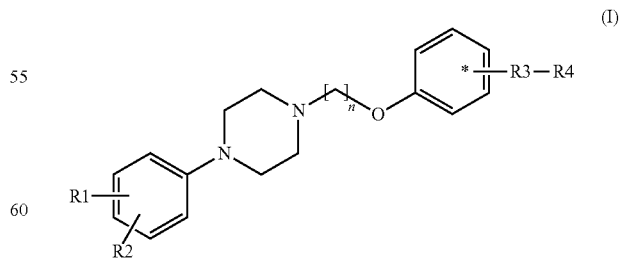

wherein,
R1, R2, R3, R4, and n are as previously defined.

The pharmaceutically acceptable salts thereof represented by Formula (XI) as below can be obtained by treating a phenyl piperazine compound of Formula (I) with an anhydrous acid in a solution without further purification.

This procedure is summarized as set forth in Reaction Scheme (II) below.

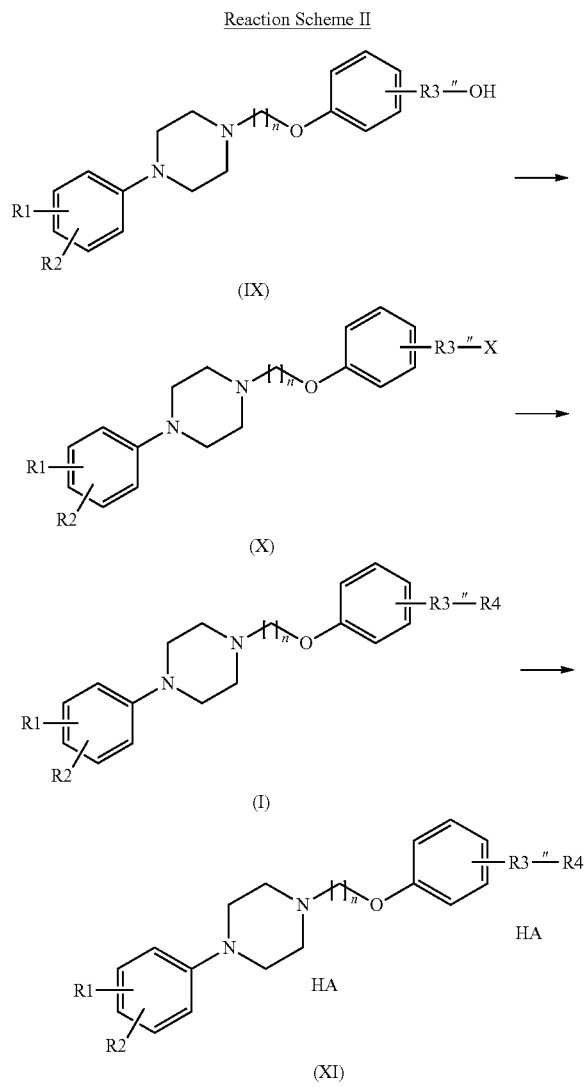

Details of the reaction conditions described in Reaction Scheme II are as follows. For the conversion of the compounds having hydroxy group (IX) to the compound (X), the concentration of the compounds having hydroxy group (IX) may be about 0.005 to about 0.1 moles with thionyl chloride ranging from about 1.0 to about 1.5 equivalents. This reaction may be carried out at a temperature of about 0° C. The resulting product may be purified by column chromatography. The resulting compound (X) may be treated with about 2.0 to about 3.0 equivalents of dialkylamines, aromatic amine, heteroaromatic amine, heterocyclic ring, or heteroaromatic ring at a reflux to give the compound of the General Formula (I). For this coupling reaction, tetrahydrofuran, acetonitrile, a halogenated hydrocarbon solvent such as dichloromethane and chloroform, or a mixture thereof may be used.

In Reaction Scheme II, HA represents an acid that is capable of forming a pharmacologically useful salt with the basic nitrogen atom. Specific examples of the anhydrous acid used for the preparation of the compound (XI) include, without limitation, hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid, hydroxyethane sulfonic acid, and the like. For additional acids, one can refer to "Pharmaceutical Salts", J. Pharm. Sci., 1977; 66(1): 1-19. This preparation may be executed in a reaction media that can be exemplified by an ethereal solvent such as tetrahydrofuran, an alcoholic solvent such as methanol, an ester solvent such as ethyl acetate, a halogenated hydrocarbon solvent, and mixtures thereof. In one embodiment, an ethereal solvent is recommended as an addition solution, including ethyl ether, propyl ether, isopropyl ether, butyl ether, and isobutyl ether. The concentration of the compound (I) may be in the order of about 0.01 to about 5 moles.

In another embodiment of the present invention, the present invention provides a pharmaceutical composition including an effective amount of phenyl piperazine compounds represented by Formula (I) for treating at least one of depression and anxiety.

In a further embodiment of the present invention, the present invention provides a method of treating at least one of depression and anxiety in a mammal comprising administering to a mammal in need thereof an effective amount of the piperazine compounds represented by Structural Formula (I), alone or in combination with a pharmaceutically acceptable carrier or excipient.

The activity of the compounds of the present invention was examined through the Mouse Tail Suspension and Marble Burying Test.

In therapeutic use as agents for depression and anxiety the compounds of the present invention are used, alone or in combination with a pharmaceutically acceptable carrier or excipient. Standard pharmaceutical formulation techniques may be used, such as those disclosed in *Remington's Pharmaceutical Sciences*, Mack Publishing Company, Easton, Pa. (1990). The compounds of the present invention may be administered orally or parentally, neat or in combination with conventional pharmaceutical carriers. "Carrier" means one or more compatible substances that are suitable for administration to a mammal. Carrier includes solid or liquid fillers, diluents, hydrotopes, surface-active agents, and encapsulating substances. "Compatible" means that the components of the composition are capable of being commingled with the piperazine compounds represented by Structural Formula (I), and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both.

The choice of carrier depends on the route by which the piperazine compounds represented by Structural Formula (I) will be administered and the form of the composition. The composition may be in a variety of forms, suitable, for example, for systemic administration (e.g., oral, rectal, nasal, sublingual, buccal, or parenteral).

The exact amounts of each component in the pharmaceutical composition depend on various factors. The amount of the piperazine compound represented by Structural Formula (I) depends on the binding affinity ($IC_{50}$) of the medicament selected. The amount of the carrier employed in conjunction with the medicament is sufficient to provide a practical quantity of material for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Applicable solid carriers can include, without limitation, one or more substances which may also act as flavoring agents, lubricants, solubilizers, suspending agents, fillers, glidants, compression aids, binders, tablet-disintegrating agents, or encapsulating materials. In powders, the carrier may be a finely divided solid that may be in admixture with the finely divided active ingredient. In tablets, the active ingredient may be mixed with a carrier having suitable compression properties in suitable proportions and compacted in the shape and size desired. The powders and tablets may contain up to about 99% of the active ingredient.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins. Liquid carriers may be used in preparing solutions, suspensions, emulsions, syrups, and elixirs.

The active ingredient of this invention may be dissolved or suspended in a pharmaceutically acceptable liquid carrier such as water, an organic solvent, a mixture of both, or pharmaceutically acceptable oils or fats. The liquid carrier may contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g., cellulose derivatives such as, without limitation, a sodium carboxymethyl cellulose solution), alcohols (including, without limitation, monohydric alcohols and polyhydric alcohols, e.g., glycols) and their derivatives, and oils (e.g., without limitation, fractionated coconut oil and arachis oil).

For parenteral administration the carrier can also be an oily ester such as ethyl oleate and isopropyl myristate. Sterile liquid carriers are used in sterile liquid form compositions for parenteral administration. Liquid pharmaceutical compositions that are sterile solutions or suspensions can be utilized by, for example, intramuscular, intraperitoneal, or subcutaneous injection. Sterile solutions can also be administered intravenously.

Oral administration may be either in liquid or solid composition form. In one embodiment, the pharmaceutical compositions containing the present compounds are in unit dosage form, e.g., as tablets or capsules. In such form, the composition may be sub-divided in unit dosages containing appropriate quantities of the active ingredients. The unit dosage forms can be packaged compositions, for example, packaged powders, vials, ampoules, prefilled syringes or sachets containing liquids. Alternatively, the unit dosage form can be, for example, a capsule or tablet itself, or it can be the appropriate number of any such compositions in package form. The therapeutically effective dosage to be used may be varied or adjusted by the physician and generally ranges from about 0.5 mg to about 750 mg, according to the specific condition(s) being treated and the size, age, and response pattern of the patient.

An effective amount of a compound according to the present invention will vary with the particular condition being treated, the age and physical condition of the patient being treated, the severity of the condition, the duration of treatment, the nature of concurrent therapy, the route of administration, the particular pharmaceutically-acceptable carrier utilized, and like factors within the knowledge and expertise of the attending physician. The compounds of the present invention may be administered to patients at a dosage of from about 0.7 to about 7000 mg per day, particularly about 1.0 to about 1000 mg. For example, for a normal human adult with a body weight of approximately 70 kg, the administration amount is translated into a daily dose of about 0.01 to about 100 mg per kg of body weight. The specific dosage employed, however, may vary depending upon the requirements of the patient, the severity of the patient's condition, and the activity of the compound. The determination of optimum dosages for a particular situation may be clinically done and is within the skill of the art. While these dosages are based upon a daily administration rate, the compounds of the present invention may also be administered at other intervals, such as twice per day, twice weekly, once weekly, or once a month. One of ordinary skill in the art would be able to calculate suitable effective amounts for other intervals of administration.

The exact amounts of each component in the pharmaceutical composition depend on various factors. The amount of the piperazine compound added to the pharmaceutical composition is dependent on the IC50 of the compound, typically expressed in nanomolar (nM) units. For example, if the IC50 of the medicament is 1 nM, the amount of the piperazine compound will be from about 0.001 to about 0.3%. If the IC50 of the medicament is 10 nM, the amount of the piperazine compound will be from about 0.01 to about 1%. If the IC50 of the medicament is 100 nM, the amount of the piperazine compound will be from about 0.1 to about 10%. If the IC50 of the medicament is 1000 nM, the amount of the piperazine compound will be 1 to 100%, preferably 5% to 50%. If the amount of the piperazine compound is outside the ranges specified above (i.e., lower), efficacy of the treatment may be reduced. One skilled in the art understands how to calculate and understand an IC50. The remainder of the composition, up to 100%, may be a pharmaceutically acceptable carrier or excipient.

A better understanding of the present invention may be obtained in light of the following examples to illustrate, but are not to be construed to limit, the present invention.

Example 1

1-[4-(4-imidazol-1-ylmethyl-phenoxy)-butyl]-4-(2-methoxy-phenyl)-piperazine

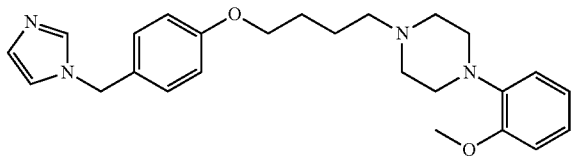 [SMILES: COc1ccccc1N1CCN(CCCCOc2ccc(Cn3ccnc3)cc2)CC1]

A mixture of 4-hydroxybenzaldehyde (5 mmol), 1-bromo-4-chlorobutane (5 mmol), and potassium carbonate (15 mmol) was refluxed in 100 ml of acetone for 6 h. This solution was then concentrated on a rotary evaporator and diluted with ethyl acetate. This mixture was then washed with brine, and the resulting organic layer was dried and purified by column chromatography. This was dissolved in methanol (50 ml) and was added with sodium borohydride (10 mmol) at 25° C. This mixture was stirred at 25° C. for 2 h. This solution was then concentrated in a rotary evaporator and diluted with methylene chloride, then washed with brine, and the resulting organic layer was dried and concentrated in vacuo. The crude product was dissolved in isopropanol (50 ml) and was added with 1-(2-methoxyphenyl)-piperazine (5 mmol), sodium carbonate (15 mmol), and potassium iodide (5 mmol) at 25° C., and the reaction mixture was refluxed for 12 h. This solution was then concentrated on a rotary evaporator and diluted with methylene chloride, then washed with brine, and the resulting organic layer was dried and purified by column chromatography. This product was dissolved in CHCl3 (30 ml) and was added with pyridine and thionyl chloride (5 mmol) at 0° C., then stirred at room temperature for 16 h, and water was added to terminate the reaction. The organic layer was extracted 3 times with dichloromethane, dried, and concentrated in vacuo. The residue was purified by column chromatography. This was dissolved in acetonitrile (30 ml) and was added with imidazole (6 mmol), potassium carbonate (15 mmol), and potassium iodide (5 mmol) at 25° C., and the reaction mixture was refluxed for 12 h. This solution was then concentrated in a rotary evaporator and diluted with methylene chloride, then washed with brine, and the resulting organic layer was dried and purified by column chromatography. The resulting 1-[4-(4-imidazole-1-ylmethyl-phenoxy)-butyl]-4-(2-methoxy-phenyl)-piperazine was dissolved in dichloromethane and the solution was treated with a solution of HCl in ethyl ether. The resulting precipitate was filtered to give 1-[4-(4-imidazole-1-ylmethyl-phenoxy)-butyl]-4-(2-methoxy-phenyl)-piperazine hydrochloride.

$^1$H-NMR (CDCl$_3$, 200 MHz) δ 11.1 (br, 1H), 7.5 (s, 1H), 7.3 (s, 1H), 7.2 (m, 2H), 6.9 (m, 7H), 5.0 (s, 2H), 4.0 (t, 2H), 3.8 (s, 3H), 3.2 (m, 4H), 2.7 (m, 4H), 2.5 (t, 2H), 1.8 (m, 4H)

Example 2

1-(2-methoxy-phenyl)-4-[4-(4-[1,2,4]triazol-1-ylmethyl-phenoxy)-butyl]-piperazine

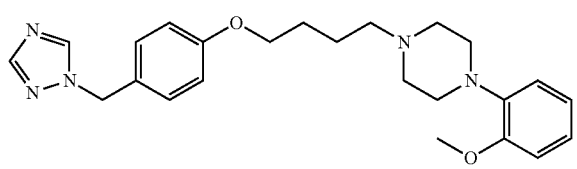 [SMILES: COc1ccccc1N1CCN(CCCCOc2ccc(Cn3cncn3)cc2)CC1]

The procedure given in Example 1 was followed using 1H-1,2,4-triazole as reactants, instead of imidazole, to give 1-(2-methoxy-phenyl)-4-[4-(4-[1,2,4]triazole-1-ylmethyl-phenoxy)-butyl]-piperazine.

$^1$H-NMR (CDCl$_3$, 200 MHz) δ 8.1 (s, 1H), 8.0 (s, 1H), 7.2 (m, 2H), 6.9 (m, 6H), 5.2 (s, 2H), 4.0 (t, 2H), 3.8 (s, 3H), 3.2 (m, 4H), 2.7 (m, 4H), 2.5 (t, 2H), 1.8 (m, 4H)

Example 3

1-(2-methoxy-phenyl)-4-[4-(4-tetrazol-1-ylmethyl-phenoxy)-butyl]-piperazine

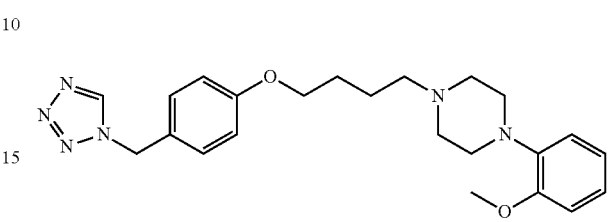

The procedure given in Example 1 was followed using 1H-tetrazole as reactants, instead of imidazole, to give 1-(2-methoxy-phenyl)-4-[4-(4-tetrazol-1-ylmethyl-phenoxy)-butyl]-piperazine.

$^1$H-NMR (CDCl$_3$, 200 MHz) δ 8.6 (s, 1H), 7.2 (m, 2H), 7.0 (m, 6H), 5.6 (s, 2H), 4.0 (t, 2H), 3.8 (s, 3H) 3.2 (m, 4H), 2.9 (m, 4H), 2.7 (t, 2H), 1.9 (m, 4H)

Example 4

1-(2-methoxy-phenyl)-4-[4-(4-tetrazol-2-ylmethyl-phenoxy)-butyl]-piperazine

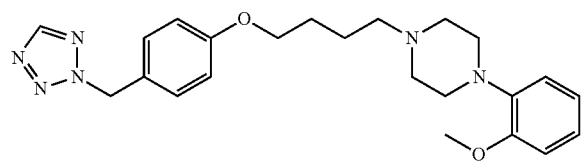 [SMILES: COc1ccccc1N1CCN(CCCCOc2ccc(Cn3ncnn3)cc2)CC1]

The procedure given in Example 1 was followed using 1H-tetrazole as reactants, instead of imidazole, to give 1-(2-methoxy-phenyl)-4-[4-(4-tetrazol-2-ylmethyl-phenoxy)-butyl]-piperazine.

$^1$H-NMR (CDCl$_3$, 200 MHz) δ 8.6 (s, 1H), 7.2 (m, 2H), 7.0 (m, 6H), 5.8 (s, 2H), 4.0 (t, 2H), 3.8 (s, 3H) 3.2 (m, 4H), 2.9 (m, 4H), 2.7 (t, 2H), 1.9 (m, 4H)

Example 5

1-[4-(3-imidazol-1-ylmethyl-phenoxy)-butyl]-4-(2-methoxy-phenyl)-piperazine-hydrochloride

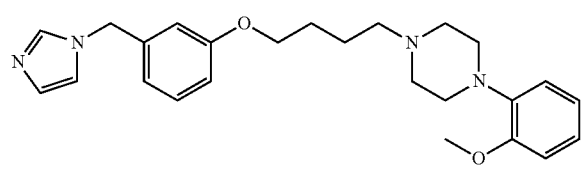 [SMILES: COc1ccccc1N1CCN(CCCCOc2cccc(Cn3ccnc3)c2)CC1]

A mixture of 3-hydroxybenzaldehyde (5 mmol), 1-bromo-4-chlorobutane (5 mmol), and potassium carbonate (15 mmol) was refluxed in 100 ml of acetone for 6 h. This solution was then concentrated in a rotary evaporator and diluted with ethyl acetate, then washed with brine, and the resulting organic layer was dried and purified by column chromatography. This was dissolved in methanol (50 ml) and was added with sodium borohydride (10 mmol) at 25° C., and was stirred at 25° C. for 2 h. This solution was then concentrated in a rotary evaporator and diluted with methylene chloride, then washed with brine, and the resulting organic layer was dried and concentrated in vacuo. The crude product was dissolved in isopropanol (50 ml) and was added with 1-(2-methoxyphenyl)-piperazine (5 mmol), sodium carbonate (15 mmol), and potassium iodide (5 mmol) at 25° C., and the reaction mixture was refluxed for 12 h. This solution was then concentrated in a rotary evaporator and diluted with methylene chloride, then washed with brine, and the resulting organic layer was dried and purified by column chromatography. This product was dissolved in CHCl$_3$ (30 ml) and was added with pyridine and thionyl chloride (5 mmol) at 0° C., and then the resulting reaction mixture was stirred at room temperature for 16 h, and water was added to terminate the reaction. The organic layer was extracted 3 times with dichloromethane, then dried and concentrated in vacuo, and the residue was purified by column chromatography. This was dissolved in acetonitrile (30 ml) and was added with imidazole (6 mmol), potassium carbonate (15 mmol), and potassium iodide (5 mmol) at 25° C., and the reaction mixture was refluxed for 12 h. This solution was then concentrated in a rotary evaporator and diluted with methylene chloride, then washed with brine, and the resulting organic layer was dried and purified by column chromatography. The resulting 1-[4-(3-imidazole-1-ylmethyl-phenoxy)-butyl]-4-(2-methoxy-phenyl)-piperazine was dissolved in dichloromethane and the solution was treated with a solution of HCl in ethyl ether. The resulting precipitate was filtered to give 1-[4-(3-imidazol-1-ylmethyl-phenoxy)-butyl]-4-(2-methoxy-phenyl)-piperazine hydrochloride.

$^1$H-NMR (DMSO, 200 MHz) δ 11.6 (br, 1H), 9.5 (s, 1H), 7.8 (s, 1H), 7.6 (s, 1H), 7.2 (m, 2H), 7.0 (m, 6H), 5.4 (s, 2H), 4.0 (t, 2H), 3.8 (s, 3H), 3.6-3.2 (m, 10H), 2.0 (m, 2H), 1.8 (m, 2H)

Example 6

1-(2-methoxy-phenyl)-4-[4-(3-[1,2,4]triazol-1-ylmethyl-phenoxy)-butyl]-piperazine hydrochloride

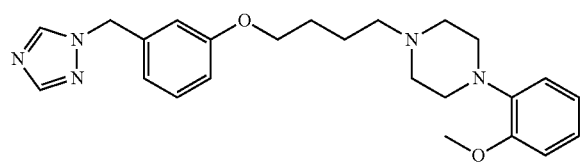 [SMILES: COc1ccccc1N1CCN(CCCCOc2cccc(Cn3cncn3)c2)CC1]

The procedure given in Example 5 was followed using 1H-1,2,4-triazole as reactants, instead of imidazole, to give 1-(2-methoxy-phenyl)-4-[4-(3-[1,2,4]triazol-1-ylmethyl-phenoxy)-butyl]-piperazine.

$^1$H-NMR (DMSO, 200 MHz) δ 11.6 (br, 1H), 9.5 (s, 1H), 8.5 (s, 1H), 7.2 (m, 2H), 7.0 (m, 6H), 5.4 (s, 2H), 4.0 (t, 2H), 3.8 (s, 3H), 3.6-3.2 (m, 10H), 2.0 (m, 2H), 1.8 (m, 2H)

Example 7

1-(2-methoxy-phenyl)-4-[4-(3-tetrazol-1-ylmethyl-phenoxy)-butyl]-piperazine hydrochloride

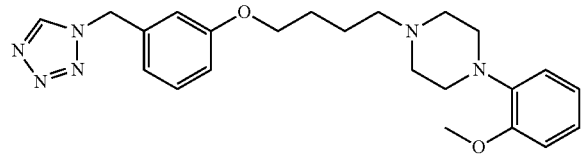 [SMILES: COc1ccccc1N1CCN(CCCCOc2cccc(Cn3cnnn3)c2)CC1]

The procedure given in Example 5 was followed using 1H-tetrazole as reactants, instead of imidazole, to give 1-(2-methoxy-phenyl)-4-[4-(3-tetrazol-1-ylmethyl-phenoxy)-butyl]-piperazine.

$^1$H-NMR (DMSO, 200 MHz) δ 10.8 (br, 1H), 9.6 (s, 1H), 7.2 (m, 2H), 7.0 (m, 6H), 5.9 (s, 2H), 4.0 (t, 2H), 3.8 (s, 3H), 3.6 (m, 4H), 3.2 (m, 6H), 2.0 (m, 2H), 1.8 (m, 2H)

Example 8

1-(2-methoxy-phenyl)-4-[4-(3-tetrazol-2-ylmethyl-phenoxy)-butyl]-piperazine hydrochloride

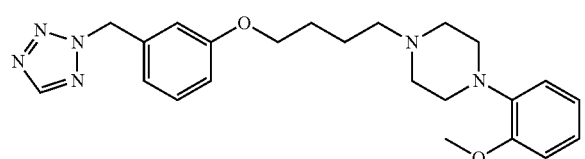

The procedure given in Example 5 was followed using 1H-tetrazole as reactants, instead of imidazole, to give 1-(2-methoxy-phenyl)-4-[4-(3-tetrazol-2-ylmethyl-phenoxy)-butyl]-piperazine.

$^1$H-NMR (DMSO, 200 MHz) δ 10.8 (br, 1H), 9.0 (s, 1H), 7.2 (m, 2H), 7.0 (m, 6H), 5.9 (s, 2H), 4.0 (t, 2H), 3.8 (s, 3H), 3.6 (m, 4H), 3.2 (m, 6H), 2.0 (m, 2H), 1.8 (m, 2H)

Example 9

1-(4-{4-[4-(2-methoxy-phenyl)-piperazin-1-yl]-butoxy}-benzyl)-1H-benzoimidazole

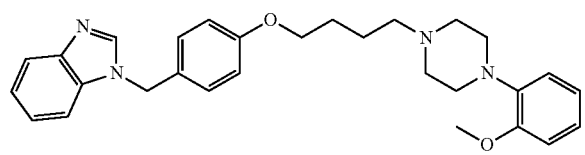 [SMILES: COc1ccccc1N1CCN(CCCCOc2ccc(Cn3cnc4ccccc43)cc2)CC1]

The procedure given in Example 1 was followed using 1H-benzoimidazole as reactants, instead of imidazole, to give 1-(4-{4-[4-(2-methoxy-phenyl)-piperazin-1-yl]-butoxy}-benzyl)-1H-benzoimidazole.

¹H-NMR (CDCl₃, 200 MHz) δ 8.0 (s, 1H), 7.8 (m, 1H), 7.3 (m, 3H), 7.2 (m., 2H), 7.0 (m, 6H), 5.3 (s, 2H), 4.0 (t, 2H), 3.8 (s, 3H), 3.1 (m, 4H), 2.7 (m, 4H), 2.5 (t, 2H), 1.8H (m, 4H)

Example 10

1-(2-Methoxy-phenyl)-4-{4-[4-(2-methyl-imidazol-1-ylmethyl)-phenoxy]-butyl}-piperazine

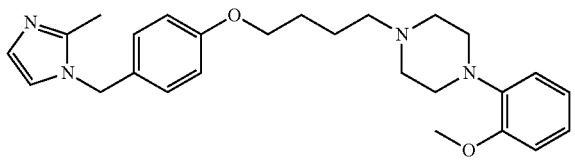 [SMILES: COc1ccccc1N1CCN(CCCCOc2ccc(Cn3ccnc3C)cc2)CC1]

The procedure given in Example 1 was followed using 2-methyl-imidazole as reactants, instead of imidazole, to give 1-(2-Methoxy-phenyl)-4-{4-[4-(2-methyl-imidazol-1-ylmethyl)-phenoxy]-butyl}-piperazine.
¹H-NMR (CDCl₃, 200 MHz) δ 7.1~6.8 (m, 10H), 5.0 (s, 2H), 4.0 (t, 2H), 3.8 (s, 3H), 3.2 (m, 4H), 2.7 (m, 4H), 2.5 (t, 2H), 2.2 (s, 3H), 1.8 (m, 4H)

Example 11

1-(2-methoxy-phenyl)-4-[4-(4-[1,2,3]triazol-2-ylmethyl-phenoxy)-butyl]-piperazine

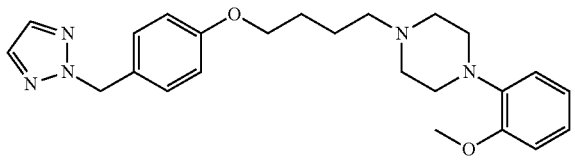 [SMILES: COc1ccccc1N1CCN(CCCCOc2ccc(Cn3nccn3)cc2)CC1]

The procedure given in Example 1 was followed using 1H-1,2,3-triazole as reactants, instead of imidazole, to give 1-(2-methoxy-phenyl)-4-[4-(4-[1,2,3]triazole-2-ylmethyl-phenoxy)-butyl]-piperazine.
(CDCl₃, 200 MHz) δ 7.6 (s, 2H), 7.2 (m, 2H), 6.9 (m, 6H), 5.6 (s, 2H), 4.0 (t, 2H), 3.8 (s, 3H), 3.2 (m, 4H), 2.7 (m, 4H), 2.5 (t, 2H), 1.8 (m, 4H)

Example 12

1-(2-methoxy-phenyl)-4-[4-(4-[1,2,3]triazol-1-ylmethyl-phenoxy)-butyl]-piperazine

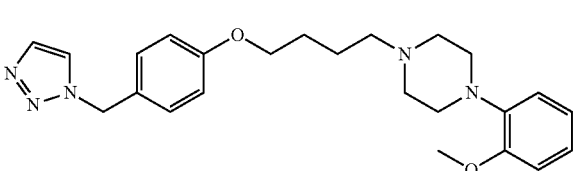

The procedure given in Example 1 was followed using 1H-1,2,3-triazole as reactants, instead of imidazole, to give 1-(2-methoxy-phenyl)-4-[4-(4-[1,2,3]triazole-1-ylmethyl-phenoxy)-butyl]-piperazine.

¹H-NMR (CDCl₃, 200 MHz) δ 7.7 (s, 1H), 7.4 (s, 1H), 7.2 (m, 2H), 6.9 (m, 6H), 5.5 (s, 2H), 4.0 (t, 2H), 3.8 (s, 3H), 3.2 (m, 4H), 2.7 (m, 4H), 2.5 (t, 2H), 1.8 (m, 4H)

Example 13

1-(4-{4-[4-(2-Methoxy-phenyl)-piperazin-1-yl]-butoxy}-benzyl)-1H-indazole

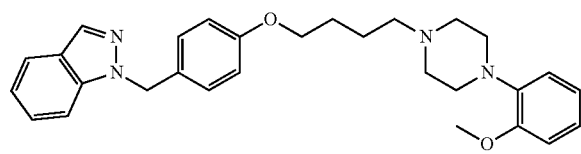 [SMILES: COc1ccccc1N1CCN(CCCCOc2ccc(Cn3ncc4ccccc43)cc2)CC1]

The procedure given in Example I was followed using 1H-Indazole as reactants, instead of imidazole, to give 1-(4-{4-[4-(2-methoxy-phenyl)-piperazin-1-yl]-butoxy}-benzyl)-1H-indazole.
¹H-NMR (CDCl₃, 200 MHz) δ 8.1 (s, 1H), 7.7 (m, 1H), 7.3 (m, 3H), 7.2 (m., 2H), 7.0 (m, 6H), 5.3 (s, 2H), 4.0 (t, 2H), 3.8 (s, 3H), 3.1 (m, 4H), 2.7 (m, 4H), 2.5 (t, 2H), 1.8 (m, 4H)

Example 14

1-(4-{4-[4-(2-Methoxy-phenyl)-piperazin-1-yl]-butoxy}-benzyl)-1H-benzotriazole

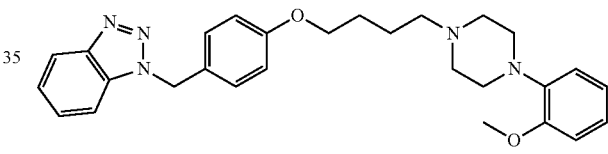

The procedure given in Example 1 was followed using benzotriazole as reactants, instead of imidazole, to give 1-(4-{4-[4-(2-Methoxy-phenyl)-piperazin-1-yl]-butoxy}-benzyl)-1H-benzotriazole.
¹H-NMR (CDCl₃, 200 MHz) δ 8.1 (m, 1H), 7.4~7.2 (m, 5H), 7.0~6.8 (m, 6H), 5.8 (s, 2H), 4.0 (t, 2H), 3.8 (s, 3H), 3.1 (m, 4H), 2.7 (m, 4H), 2.5 (t, 2H), 1.8 (m, 4H)

Example 15

1-(2-methoxy-phenyl)-4-{4-[4-(5-phenyl-tetrazol-2-ylmethyl)-phenoxy]-butyl}-piperazine

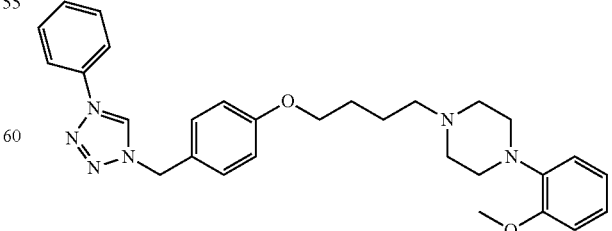

The procedure given in Example 1 was followed using 5-phenyl-1H-tetrazole as reactants, instead of imidazole, to give 1-(2-methoxy-phenyl)-4-{4-[4-(5-phenyl-tetrazol-2-yl-methyl)-phenoxy]-butyl}-piperazine.

¹H-NMR (CDCl₃, 200 MHz) δ 8.2 (m, 2H), 7.6 (m, 5H), 7.2~7.0 (m., 6H), 5.8 (s, 2H), 4.0 (t, 2H), 3.8 (s, 3H), 3.1 (m, 4H), 2.7 (m, 4H), 2.5 (t, 2H), 1.8 (m, 4H)

Example 16

1-(2-methoxy-phenyl)-4-{4-[4-(5-phenyl-tetrazol-1-ylmethyl)-phenoxy]-butyl}-piperazine

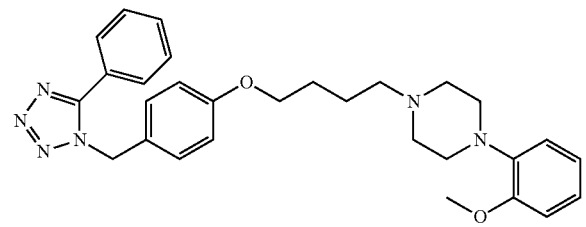 [SMILES: COc1ccccc1N1CCN(CCCCOc2ccc(Cn3nnnc3-c3ccccc3)cc2)CC1]

The procedure given in Example 1 was followed using 5-phenyl-1H-tetrazole as reactants, instead of imidazole, to give 1-(2-methoxy-phenyl)-4-{4-[4-(5-phenyl-tetrazol-1-yl-methyl)-phenoxy]-butyl}-piperazine.

¹H-NMR (CDCl₃, 200 MHz) δ 7.6 (m, 4H), 7.2 (m., 3H), 6.9 (m, 6H), 5.6 (s, 2H), 4.0 (t, 2H), 3.8 (s, 3H), 3.1 (m, 4H), 2.7 (m, 4H), 2.5 (t, 2H), 1.8 (m, 4H)

Example 17

1-(2-methoxy-phenyl)-4-{4-[4-(5-methyl-tetrazol-2-ylmethyl)-phenoxy]-butyl}-piperazine

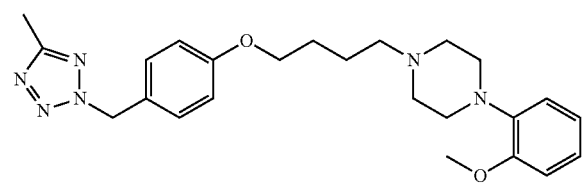 [SMILES: COc1ccccc1N1CCN(CCCCOc2ccc(Cn3nnc(C)n3)cc2)CC1]

The procedure given in Example 1 was followed using 5-methyl-1H-tetrazole as reactants, instead of imidazole, to give 1-(2-methoxy-phenyl)-4-{4-[4-(5-methyl-tetrazol-2-yl-methyl)-phenoxy]-butyl}-piperazine.

¹H-NMR (CDCl₃, 200 MHz) δ 7.4 (m, 2H), 7.0 (m, 6H), 5.6 (s, 2H), 4.0 (t, 2H), 3.8 (s, 3H), 3.1 (m, 4H), 2.7 (m, 4H), 2.5 (t, 2H), 2.5 (s, 3H), 1.8 (m, 4H)

Example 18

1-(2-methoxy-phenyl)-4-{4-[4-(5-methyl-tetrazol-1-ylmethyl)-phenoxy]-butyl}-piperazine

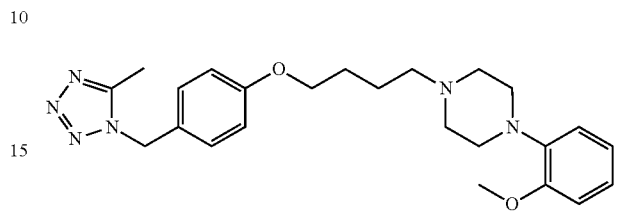

The procedure given in Example 1 was followed using 5-methyl-1H-tetrazole as reactants, instead of imidazole, to give 1-(2-methoxy-phenyl)-4-{4-[4-(5-methyl-tetrazol-1-yl-methyl)-phenoxy]-butyl}-piperazine.

¹H-NMR (CDCl₃, 200 MHz) δ 7.2 (m, 2H), 7.0 (m, 6H), 5.4 (s, 2H), 4.0 (t, 2H), 3.8 (s, 3H), 3.1 (m, 4H), 2.7 (m, 4H), 2.5 (t, 2H), 2.5 (s, 3H), 1.8 (m, 4H)

Example 19

(4-{4-[4-(2-methoxy-phenyl)-piperazin-1-yl]-butoxy}-benzyl)-dimethyl-amine dihydrochloride

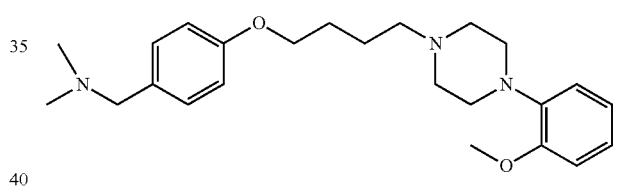

The procedure given in Example 1 was followed using dimethyl amine as reactants, instead of imidazole, to give (4-{4-[4-(2-methoxy-phenyl)-piperazin-1-yl]-butoxy}-benzyl)-dimethyl-amine dihydrochloride.

¹H-NMR (DMSO, 200 MHz) δ 11.3 (br, 1H), 11.1 (br, 1H), 7.5 (m, 2H), 7.0 (m, 6H), 4.2 (m, 2H), 4.0 (t, 2H), 3.8 (s, 3H), 3.6 (m, 4H), 3.2 (m, 6H), 2.6 (m, 6H), 1.8 (m, 4H)

Example 20

1-(2-methoxy-phenyl)-4-[4-(4-piperidin-1-ylmethyl-phenoxy)-butyl]-piperazine

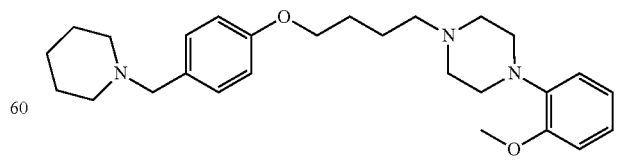

The procedure given in Example 1 was followed using piperidine as reactants, instead of imidazole, to give 1-(2-methoxy-phenyl)-4-[4-(4-piperidin-1-ylmethyl-phenoxy)-butyl]-piperazine.

¹H-NMR (CDCl₃, 200 MHz) δ 7.2 (m, 2H), 6.9 (m, 6H), 4.0 (t, 2H), 3.8 (s, 3H), 3.4 (s, 2H), 3.2 (m, 4H), 2.7 (m, 4H), 2.5 (t, 2H), 2.4 (m, 4H), 1.8 (m, 4H), 1.6 (m, 4H), 1.4 (m, 2H)

Example 21

(4-{4-[4-(2-methoxy-phenyl)-piperazin-1-yl]-butoxy}-benzyl)-phenyl-amine

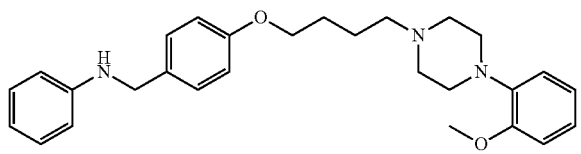 [SMILES: COc1ccccc1N1CCN(CCCCOc2ccc(CNc3ccccc3)cc2)CC1]

The procedure given in Example 1 was followed using aniline as reactants, instead of imidazole, to give (4-{4-[4-(2-methoxy-phenyl)-piperazin-1-yl]-butoxy}-benzyl)-phenyl-amine.
¹H-NMR (CDCl₃, 200 MHz) δ 7.2 (m, 2H), 7.0 (m, 6H), 6.8 (m, 5H), 4.3 (s, 2H), 4.0 (t, 2H), 3.8 (s, 3H), 3.6 (s, 1H), 3.2 (m, 4H), 2.7 (m, 4H), 2.5 (t, 2H), 1.8 (m, 4H)

Example 22

10663

(4-{4-[4-(2-methoxy-phenyl)-piperazin-1-yl]-butoxy}-benzyl)-thiazol-2-yl-amine

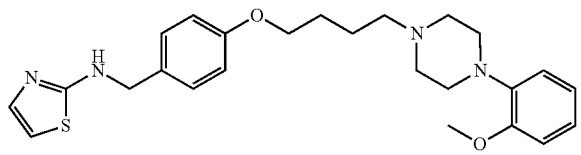 [SMILES: COc1ccccc1N1CCN(CCCCOc2ccc(CNc3nccs3)cc2)CC1]

The procedure given in Example 1 was followed using thiazol-2-ylamine as reactants, instead of imidazole, to give (4-{4-[4-(2-methoxy-phenyl)-piperazin-1-yl]-butoxy}-benzyl)-thiazol-2-yl-amine.
¹H-NMR (CDCl₃, 200 MHz) δ 7.5 (s, 1H), 7.2 (m, 2H), 7.0 (m, 6H), 6.6 (s, 1H), 4.3 (s, 2H), 4.0 (t, 2H), 3.8 (s, 3H), 3.6 (s, 1H), 3.2 (m, 4H), 2.7 (m, 4H), 2.5 (t, 2H), 1.8 (m, 4H)

Example 23

1-(2-chloro-phenyl)-4-[4-(4-[1,2,4]triazol-1-ylmethyl-phenoxy)-butyl]-piperazine

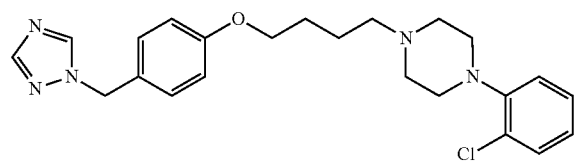 [SMILES: Clc1ccccc1N1CCN(CCCCOc2ccc(Cn3cncn3)cc2)CC1]

The procedure given in Example 1 was followed using 1-(2-chloro-phenyl)-piperazine and 1H-1,2,4-triazole as reactants, instead of 1-(2-methoxyphenyl)-piperazine and imidazole, to give 1-(2-chloro-phenyl)-4-[4-(4-[1,2,4]triazol-1-ylmethyl-phenoxy)-butyl]-piperazine.
¹H-NMR (CDCl₃, 200 MHz) δ 8.1 (s, 1H), 8.0 (s, 1H), 7.2 (m, 2H), 6.9 (m, 6H), 5.4 (s, 2H), 4.0 (t, 2H), 4.0 (t, 2H), 3.2 (m, 4H), 2.7 (m, 4H), 2.5 (t, 2H), 1.8 (m, 4H)

Example 24

1-(2-methoxy-phenyl)-4-[4-(3-[1,2,3]triazol-2-ylmethyl-phenoxy)-butyl]-piperazine

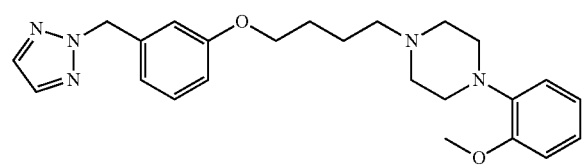 [SMILES: COc1ccccc1N1CCN(CCCCOc2cccc(Cn3nccn3)c2)CC1]

The procedure given in Example 5 was followed using 1H-1,2,3-triazole as reactants, instead of imidazole, to give 1-(2-methoxy-phenyl)-4-[4-(3-[1,2,3]triazol-2-ylmethyl-phenoxy)-butyl]-piperazine.
¹H-NMR (CDCl₃, 200 MHz) δ 7.6 (s, 2H), 7.2 (m, 2H), 6.9 (m, 6H), 5.4 (s, 2H), 4.0 (t, 2H), 3.8 (s, 3H), 3.2 (m, 4H), 2.7 (m, 4H), 2.5 (t, 2H), 1.8 (m, 4H)

Example 25

1-(2-Methoxy-phenyl)-4-[4-(3-[1,2,3]triazol-1-ylmethyl-phenoxy)-butyl]-piperazine

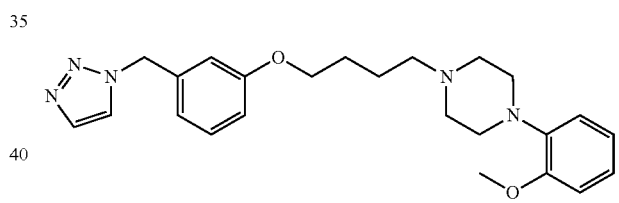

The procedure given in Example 5 was followed using 1H-1,2,3-triazole as reactants, instead of Imidazole, to give 1-(2-Methoxy-phenyl)-4-[4-(3-[1,2,3]triazol-1-ylmethyl-phenoxy)-butyl]-piperazine.
¹H-NMR (CDCl₃, 200 MHz) δ 7.7 (s, 1H), 7.4 (s, 1H), 7.2 (m, 2H), 7.0-6.8 (m, 6H), 5.5 (s, 2H), 4.0 (t, 2H), 3.8 (s, 3H), 3.1 (m, 4H), 2.7 (m, 4H), 2.5 (t, 2H), 2.5 (s, 3H), 1.8 (m, 4H)

Example 26

1-(2-Methoxy-phenyl)-4-{4-[3-(5-methyl-tetrazol-2-ylmethyl)-phenoxy]-butyl}-piperazine

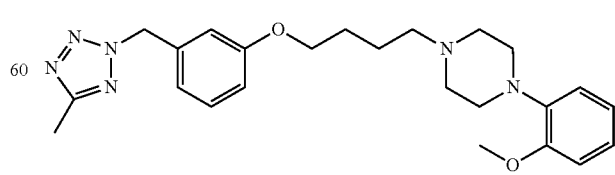

The procedure given in Example 5 was followed using 5-methyl-1H-tetrazole as reactants, instead of imidazole, to give 1-(2-Methoxy-phenyl)-4-{4-[3-(5-methyl-tetrazol-2-yl-methyl)-phenoxy]-butyl}-piperazine.

¹H-NMR (CDCl₃, 200 MHz) δ 7.6 (s, 2H), 7.2 (m, 2H), 7.0-6.8 (m, 6H), 5.5 (s, 2H), 4.0 (t, 2H), 3.8 (s, 3H), 3.1 (m, 4H), 2.7 (m, 4H), 2.5 (t, 2H), 2.5 (s, 3H), 1.8 (m, 4H)

Example 27

1-(2-methoxy-phenyl)-4-{4-[3-(5-methyl-tetrazol-1-ylmethyl)-phenoxy]-butyl}-piperazine

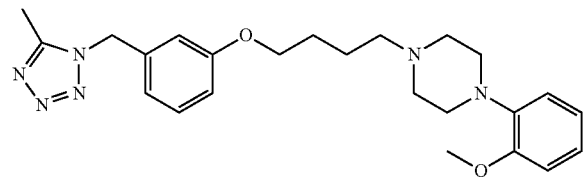 [SMILES: COc1ccccc1N1CCN(CCCCOc2cccc(Cn3nnnc3C)c2)CC1]

The procedure given in Example 5 was followed using 5-methyl-1H-tetrazole as reactants, instead of imidazole, to give 1-(2-methoxy-phenyl)-4-{4-[3-(5-methyl-tetrazol-1-yl-methyl)-phenoxy]-butyl}-piperazine.

¹H-NMR (CDCl₃, 200 MHz) δ 7.2 (m, 2H), 7.0-6.7 (m, 6H), 5.5 (s, 2H), 4.0 (t, 2H), 3.8 (s, 3H), 3.1 (m, 4H), 2.7 (m, 4H), 2.5 (t, 2H), 2.5 (s, 3H), 1.8 (m, 4H)

Example 28

(3-{4-[4-(2-methoxy-phenyl)-piperazin-1-yl]-butoxy}-benzyl)-dimethyl-amine

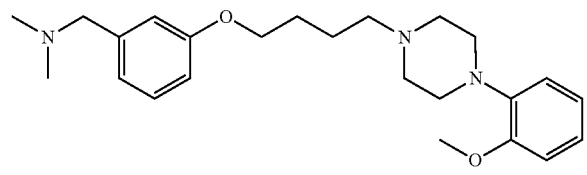 [SMILES: COc1ccccc1N1CCN(CCCCOc2cccc(CN(C)C)c2)CC1]

The procedure given in Example 5 was followed using dimethyl amine as reactants, instead of imidazole, to give (3-{4-[4-(2-methoxy-phenyl)-piperazin-1-yl]-butoxy}-benzyl)-dimethyl-amine.

¹H-NMR (CDCl₃, 200 MHz) δ 7.3 (m, 2H), 6.9 (m, 6H), 4.0 (t, 2H), 3.9 (s, 3H), 3.2 (m, 4H), 2.7 (m, 4H), 2.6 (s, 6H), 2.5 (t, 2H), 1.8 (m, 4H)

Example 29

4-(3-{4-[4-(2-methoxy-phenyl)-piperazin-1-yl]-butoxy}-benzyl)-morpholine

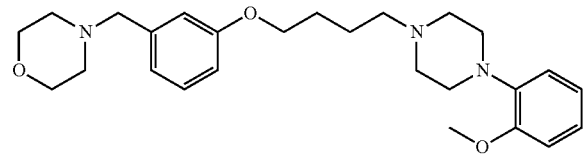 [SMILES: COc1ccccc1N1CCN(CCCCOc2cccc(CN3CCOCC3)c2)CC1]

The procedure given in Example 5 was followed using morpholine as reactants, instead of imidazole, to give 4-(3-{4-[4-(2-methoxy-phenyl)-piperazin-1-yl]-butoxy}-benzyl)-morpholine.

¹H-NMR (CDCl₃, 200 MHz) 7.2 (m, 2H), 6.9 (m, 6H), 4.1 (t, 2H), 3.9 (s, 3H), 3.7 (m, 4H), 3.5 (s, 2H), 3.2 (m, 4H), 2.8 (m, 4H), 2.6 (t, 2H), 2.5 (m, 4H), 1.8 (m, 4H)

Example 30

1-{4-[4-(4,5-dichloro-imidazol-1-ylmethyl)-phenoxy]-butyl}-4-(2-methoxy-phenyl)-piperazine

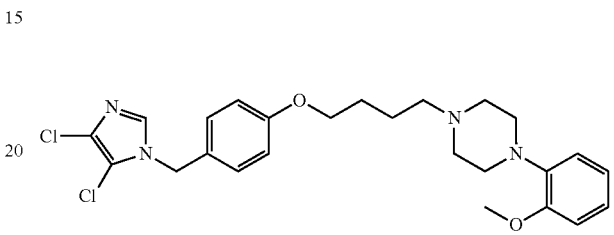

The procedure given in Example 1 was followed using 4,5-dichloro-imidazole as reactants, instead of imidazole, to give 1-{4-[4-(4,5-dichloro-imidazol-1-ylmethyl)-phenoxy]-butyl}-4-(2-methoxy-phenyl)-piperazine.

¹H-NMR (CDCl₃, 200 MHz) δ 7.4 (s. 1H), 7.2 (m, 2H), 6.9 (m, 6H), 5.0 (s, 2H), 4.0 (t, 2H), 3.8 (s, 3H), 3.2 (m, 4H), 2.7 (m, 4H), 2.5 (t, 2H), 1.8 (m, 4H)

Example 31

1-(2-chloro-phenyl)-4-[4-(4-tetrazol-2-ylmethyl-phenoxy)-butyl]-piperazine

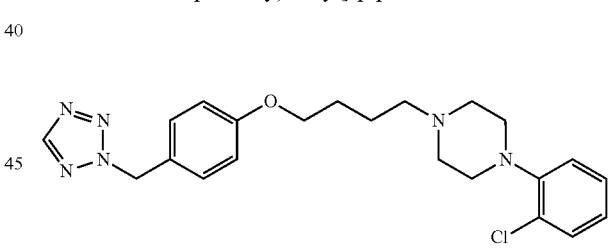

The procedure given in Example 1 was followed using 1-(2-chloro-phenyl)-piperazine and 1H-tetrazole as reactants, instead of 1-(2-methoxyphenyl)-piperazine and imidazole, to give 1-(2-chloro-phenyl)-4-[4-(4-tetrazol-2-ylmethyl-phenoxy)-butyl]-piperazine.

¹H-NMR (CDCl₃, 200 MHz) δ 8.5 (m, 1H), 7.4 (m, 4H), 7.0 (m, 2H), 6.8 (m, 2H), 5.8 (s, 2H), 4.0 (t, 2H), 3.2 (m, 4H), 2.9 (m, 4H), 2.7 (t, 2H), 1.9 (m, 4H)

Example 32

4-(4-{4-[4-(2-methoxy-phenyl)-piperazin-1-yl]-butoxy}-benzyl)-morpholine

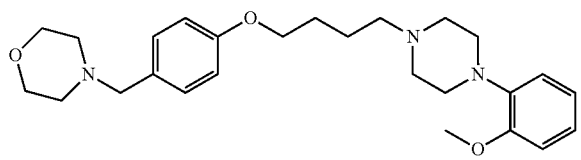 [SMILES: COc1ccccc1N1CCN(CCCCOc2ccc(CN3CCOCC3)cc2)CC1]

The procedure given in Example 1 was followed using morpholine as reactants, instead of imidazole, to give 4-(4-{4-[4-(2-methoxy-phenyl)-piperazin-1-yl]-butoxy}-benzyl)-morpholine.
¹H-NMR (CDCl₃, 200 MHz) δ 7.2 (m, 2H), 6.9 (m, 6H), 4.0 (t, 2H), 3.8 (s, 3H), 3.4 (s, 2H), 3.2 (m, 4H), 2.7 (m, 4H), 2.5 (t, 2H), 2.4 (m, 4H), 1.8 (m, 4H), 1.6 (m, 4H)

Example 33

(4-{4-[4-(2-Chloro-phenyl)-piperazin-1-yl]-butoxy}-benzyl)-dimethyl-amine

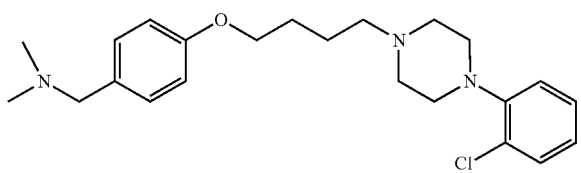 [SMILES: CN(C)Cc1ccc(OCCCCN2CCN(c3ccccc3Cl)CC2)cc1]

The procedure given in Example 1 was followed using 1-(2-chloro-phenyl)-piperazine and dimethylamine, instead of 1-(2-methoxyphenyl)-piperazine and imidazole, to give (4-{4-[4-(2-Chloro-phenyl)-piperazin-1-yl]-butoxy}-benzyl)-dimethyl-amine.
¹H-NMR (CDCl₃, 200 MHz) δ 7.3-7.1 (m, 4H), 7.1~6.8 (m, 4H), 4.2 (t, 2H), 3.4 (m, 2H), 3.1 (m, 4H), 2.7 (m, 4H), 2.5 (m, 2H), 2.4 (s, 6H), 1.8~1.7 (m, 4H)

Example 34

1-(3-fluoro-phenyl)-4-[4-(4-[1,2,4]triazol-1-ylmethyl-phenoxy)-butyl]-piperazine

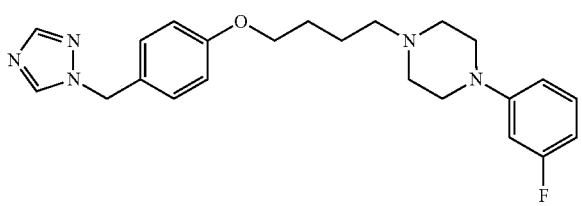 [SMILES: Fc1cccc(N2CCN(CCCCOc3ccc(Cn4cncn4)cc3)CC2)c1]

The procedure given in Example 1 was followed using 1-(3-fluoro-phenyl)-piperazine and 1H-1,2,4-triazole as reactants, instead of 1-(2-methoxyphenyl)-piperazine and imidazole, to give 1-(3-fluoro-phenyl)-4-[4-(4-[1,2,4]triazol-1-ylmethyl-phenoxy)-butyl]-piperazine.
¹H-NMR (CDCl₃, 200 MHz) δ 7.9 (s, 1H), 7.7 (s, 1H), 7.2 (m, 2H), 6.9 (m, 6H), 5.5 (s, 2H), 4.0 (t, 2H), 3.2 (m, 4H), 2.8 (m, 4H), 2.6 (t, 2H), 1.8 (m, 4H)

Example 35

1-(2-methoxy-phenyl)-4-[4-(4-4-methylpiperazine-1-ylmethyl-phenoxy)-butyl]-piperazine

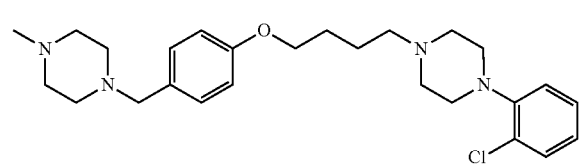 [SMILES: CN1CCN(Cc2ccc(OCCCCN3CCN(c4ccccc4Cl)CC3)cc2)CC1]

The procedure given in Example 1 was followed using 1-(2-chloro-phenyl)-piperazine and methylpiperazine, instead of instead of 1-(2-methoxyphenyl)-piperazine and imidazole, to give 1-(2-methoxy-phenyl)-4-[4-(4-4-methylpiperazine-1-ylmethyl-phenoxy)-butyl]-piperazine.
¹H-NMR (CDCl₃, 200 MHz) δ 7.3~7.1 (m, 4H), 7.1~6.8 (m, 4H), 4.3 (t, 2H), 3.4 (m, 2H), 3.1 (m, 4H), 2.7 (m, 4H), 2.6 (m, 8H,) 2.5 (m, 2H), 2.3 (s, 3H), 1.8~1.7 (m, 4H)

Example 36

1-(2,3-dichloro-phenyl)-4-[4-(4-tetrazol-2-ylmethyl-phenoxy)-butyl]-piperazine

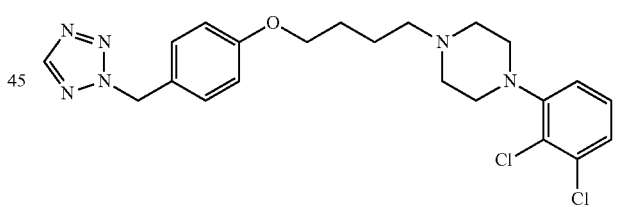

The procedure given in Example 1 was followed using 1-(2,3-dichloro-phenyl)-piperazine and 1H-tetrazole as reactants, instead of 1-(2-methoxyphenyl)-piperazine and imidazole, to give 1-(2,3-dichloro-phenyl)-4-[4-(4-tetrazol-2-ylmethyl-phenoxy)-butyl]-piperazine.

¹H-NMR (CDCl₃, 200 MHz) δ 8.5 (m, 1H), 7.4-6.8 (m, 7H), 5.8 (s, 2H), 4.0 (t, 2H), 3.2 (m, 4H), 2.9 (m, 4H), 2.7 (t, 2H), 1.9 (m, 4H)

Example 37

1-(2,3-Dichloro-phenyl)-4-{4-[4-(5-methyl-tetrazol-1-ylmethyl)-phenoxy]-butyl}-piperazine

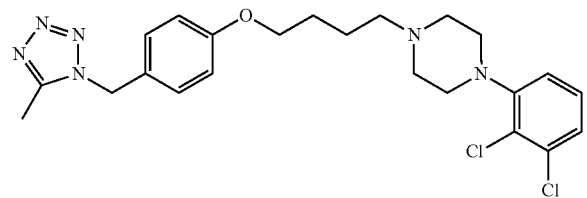 [SMILES: Cc1nnnn1Cc1ccc(OCCCCN2CCN(c3cccc(Cl)c3Cl)CC2)cc1]

The procedure given in Example 1 was followed using 1-(2,3-dichloro-phenyl)-piperazine and 5-methyl-1H-tetrazole as reactants, instead of 1-(2-methoxyphenyl)-piperazine and imidazole, to give 1-(2,3-Dichloro-phenyl)-4-{4-[4-(5-methyl-tetrazol-1-ylmethyl)-phenoxy]-butyl}-piperazine.

¹H-NMR (CDCl₃, 200 MHz) δ 7.2 (m, 2H), 7.0 (m, 5H), 5.4 (s, 2H), 4.0 (t, 2H), 3.1 (m, 4H), 2.7 (m, 4H), 2.5 (t, 2H), 2.6 (s, 3H), 1.8 (m, 4H)

Example 38

1-(2,3-Dichloro-phenyl)-4-{4-[4-(5-methyl-tetrazol-2-ylmethyl)-phenoxy]-butyl}-piperazine

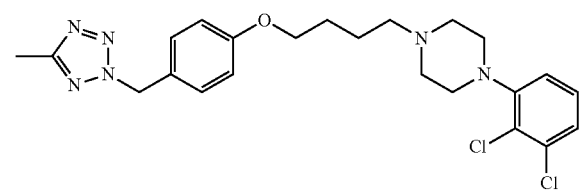 [SMILES: Cc1nnn(Cc2ccc(OCCCCN3CCN(c4cccc(Cl)c4Cl)CC3)cc2)n1]

The procedure given in Example 1 was followed using 1-(2,3-dichloro-phenyl)-piperazine and 5-methyl-1H-tetrazole as reactants, instead of 1-(2-methoxyphenyl)-piperazine and imidazole, to give 1-(2,3-Dichloro-phenyl)-4-{4-[4-(5-methyl-tetrazol-2-ylmethyl)-phenoxy]-butyl}-piperazine.

¹H-NMR (CDCl₃, 200 MHz) δ 7.2-7.0 (m, 7H), 5.6 (s, 2H), 4.0 (t, 2H), 3.1 (m, 4H), 2.7 (m, 4H), 2.5 (t, 2H), 2.5 (s, 3H), 1.8 (m, 4H)

Example 39

(4-{4-[4-(2,3-dichloro-phenyl)-piperazin-1-yl]-butoxy}-benzyl)-dimethyl-amine

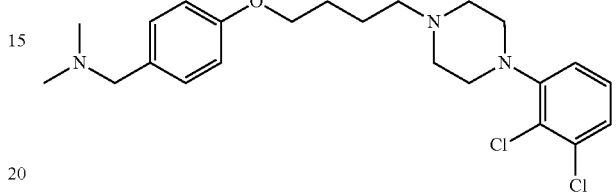

The procedure given in Example 1 was followed using 1-(2,3-dichloro-phenyl)-piperazine and dimethyl amine as reactants, instead of 1-(2-methoxyphenyl)-piperazine and imidazole, to give (4-{4-[4-(2,3-dichloro-phenyl)-piperazin-1-yl]-butoxy}-benzyl)-dimethyl-amine.

¹H-NMR (DMSO, 200 MHz) δ 11.3 (br, 1H), 11.1 (br, 1H), 7.5 (m, 2H), 7.0 (m, 5H), 4.2 (m, 2H), 4.0 (t, 2H), 3.6 (m, 4H), 3.2 (m, 6H), 2.6 (m, 6H), 1.8 (m, 4H)

Example 40

4-(4-{4-[4-(2,3-Dichloro-phenyl)-piperazin-1-yl]-butoxy}-benzyl)-morpholine

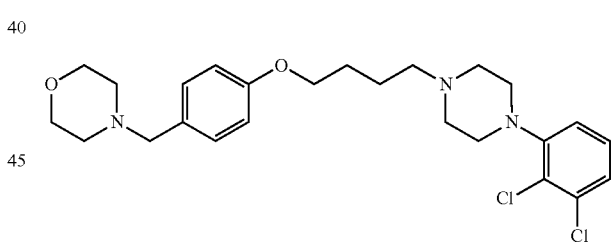

The procedure given in Example 1 was followed using 1-(2,3-dichloro-phenyl)-piperazine and morpholine, instead of 1-(2-methoxyphenyl)-piperazine and imidazole, to give 4-(4-{4-[4-(2,3-Dichloro-phenyl)-piperazin-1-yl]-butoxy}-benzyl)-morpholine ¹H-NMR (CDCl₃, 200 MHz) δ 7.2 (m, 2H), 6.9 (m, 6H), 4.2 (t, 2H), 3.7 (m, 4H), 3.5 (s, 2H), 3.2 (m, 4H), 2.8 (m, 4H), 2.6 (t, 2H), 2.5 (m, 4H), 1.8 (m, 4H)

Example 41

1-(2-methoxy-phenyl)-4-[4-(4-4-methylpiperazine-1-ylmethyl-phenoxy)-butyl]-piperazine

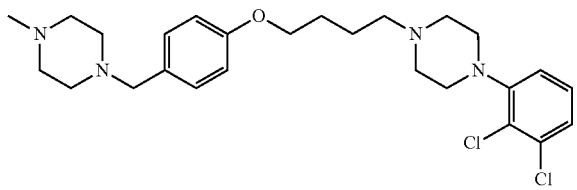 [SMILES: CN1CCN(Cc2ccc(OCCCCN3CCN(c4cccc(Cl)c4Cl)CC3)cc2)CC1]

The procedure given in Example 1 was followed using 1-(2,3-dichloro-phenyl)-piperazine and methylpiperazine, instead of 1-(2-methoxyphenyl)-piperazine and imidazole to give 1-(2-methoxy-phenyl)-4-[4-(4-4-methylpiperazine-1-ylmethyl-phenoxy)-butyl]-piperazine.

¹H-NMR (CDCl₃, 200 MHz) δ 7.3~6.8 (m, 7H), 4.3 (t, 2H), 3.4 (m, 2H), 3.1 (m, 4H), 2.7 (m, 4H), 2.6 (m, 8H,) 2.5 (m, 2H), 2.3 (s, 3H), 1.8~1.7 (m, 4H)

Example 42

1-(2-chloro-phenyl)-4-[4-(4-[1,2,3]triazol-1-ylmethyl-phenoxy)-butyl]-piperazine

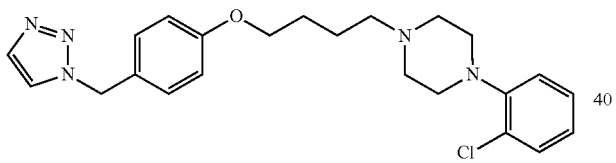

The procedure given in Example 1 was followed using 1-(2-chloro-phenyl)-piperazine and 1H-1,2,3-triazole as reactants, instead of 1-(2-methoxyphenyl)-piperazine and imidazole, to give 1-(2-chloro-phenyl)-4-[4-(4-[1,2,3]triazol-1-ylmethyl-phenoxy)-butyl]-piperazine.

¹H-NMR (CDCl₃, 200 MHz) δ 7.7 (s, 1H), 7.4 (s, 1H), 7.2 (m, 2H), 6.9 (m, 6H), 5.5 (s, 2H), 4.0 (t, 2H), 3.2 (m, 4H), 2.7 (m, 4H), 2.5 (t, 2H), 1.8 (m, 4H)

Example 43

(4-{4-[4-(2-Methoxy-phenyl)-piperazin-1-yl]-butoxy}-benzyl)-[1,3,4]thiadiazol-2-yl-amine

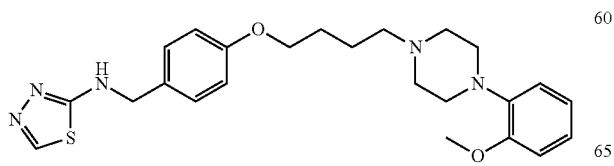

The procedure given in Example 1 was followed using [1,3,4]Thiadiazol-2-ylamine as reactants, instead of imidazole, to give (4-{4-[4-(2-Methoxy-phenyl)-piperazin-1-yl]-butoxy}-benzyl)-[1,3,4]thiadiazol-2-yl-amine.

¹H-NMR (CDCl₃, 200 MHz) δ 7.2~6.8 (m, 9H), 4.3 (s, 2H), 4.0 (t, 2H), 3.8 (s, 3H), 3.2 (m, 4H), 2.7 (m, 4H), 2.5 (t, 2H), 1.8 (m, 4H)

Example 44

1-(2,3-dichloro-phenyl)-4-[4-(4-[1,2,3]triazol-1-ylmethyl-phenoxy)-butyl]-piperazine

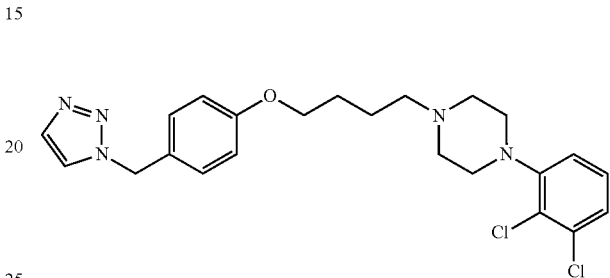

The procedure given in Example 1 was followed using 1-(2,3-dichloro-phenyl)-piperazine and 1H-1,2,3-triazole as reactants, instead of 1-(2-methoxyphenyl)-piperazine and imidazole, to give 1-(2,3-dichloro-phenyl)-4-[4-(4-[1,2,3]triazol-1-ylmethyl-phenoxy)-butyl]-piperazine.

¹H-NMR (CDCl₃, 200 MHz) δ 7.7 (s, 1H), 7.4-6.8 (m, 8H), 5.8 (s, 2H), 4.0 (t, 2H), 3.2 (m, 4H), 2.9 (m, 4H), 2.7 (t, 2H), 1.9 (m, 4H)

Example 45

(4-{4-[4-(2-Methoxy-phenyl)-piperazin-1-yl]-butoxy}-benzyl)-(5-methyl-isoxazol-3-yl)-amine

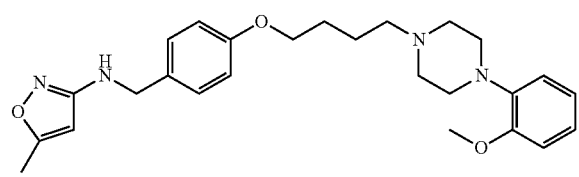 [SMILES: COc1ccccc1N1CCN(CCCCOc2ccc(CNc3cc(C)on3)cc2)CC1]

The procedure given in Example 1 was followed using 5-methyl-isoxazol-3-ylamine as reactants, instead of imidazole, to give (4-{4-[4-(2-Methoxy-phenyl)-piperazin-1-yl]-butoxy}-benzyl)-(5-methyl-isoxazol-3-yl)-amine.

¹H-NMR (CDCl₃, 200 MHz) δ 7.2-6.8 (m, 9H), 4.3 (s, 2H), 4.0 (t, 2H), 3.8 (s, 3H), 3.6 (s, 1H) 3.2 (m, 4H), 2.7 (m, 4H), 2.5 (t, 2H), 2.3 (s, 3H), 1.8 (m, 4H)

Example 46

(4-{4-[4-(2-methoxy-phenyl)-piperazin-1-yl]-butoxy}-benzyl)-(3-methyl-isoxazol-5-yl)-amine

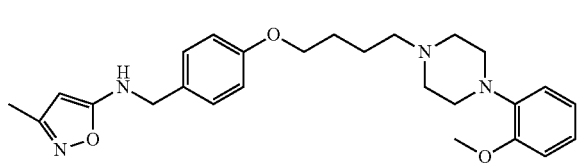 [SMILES: COc1ccccc1N1CCN(CCCCOc2ccc(CNc3cc(C)no3)cc2)CC1]

The procedure given in Example 1 was followed using 3-methyl-isoxazol-5-ylamine as reactants, instead of imidazole, to give (4-{4-[4-(2-methoxy-phenyl)-piperazin-1-yl]-butoxy}-benzyl)-(3-methyl-isoxazol-5-yl)-amine.

¹H-NMR (CDCl₃, 200 MHz) δ 7.2 (m, 2H), 7.0 (m, 6H), 6.8 (s, 1H), 4.3 (s, 2H), 4.0 (t, 2H), 3.8 (s, 3H), 3.6 (s, 1H), 3.2 (m, 4H), 2.7 (m, 4H), 2.5 (t, 2H), 2.3 (s, 3H), 1.8 (m, 4H)

Example 47

1-{4-[4-(2-imidazol-1-yl-ethyl)-phenoxy]-butyl}-4-(2-methoxy-phenyl)-piperazine

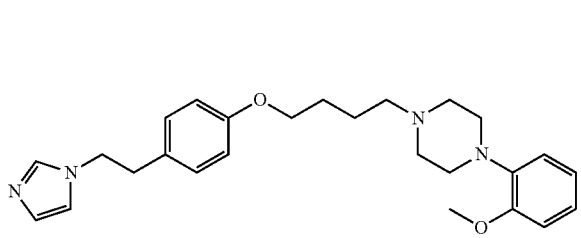 [SMILES: COc1ccccc1N1CCN(CCCCOc2ccc(CCn3ccnc3)cc2)CC1]

A mixture of 4-hydroxyphenetylalcohol (5 mmol), 1-bromo-4-chlorobutane (5 mmol), and potassium carbonate (15 mmol) was refluxed in 100 ml of acetone for 6 h. This solution was then concentrated in a rotary evaporator and diluted with ethyl acetate. This mixture was then washed with brine, and the resulting organic layer was dried and purified by column chromatography. The product was dissolved in isopropanol (50 ml) and was added with 1-(2-methoxyphenyl)-piperazine (5 mmol), sodium carbonate (15 mmol), and potassium iodide (5 mmol) at 25° C. and the reaction mixture was refluxed for 12 h. This solution was then concentrated in a rotary evaporator and diluted with methylene chloride. This mixture was then washed with brine, and the resulting organic layer was dried and purified by column chromatography. The product was dissolved in THF and was added with imidazole (15 mmol), triphenylphosphine (15 mmol), and diisopropyl azodicarboxylate (15 mmol) dropwise at 0° C. and warmed to room temperature. After 2 h, the solvent was removed and the residue was washed with brine, and then purified by column chromatography.

¹H-NMR (CDCl₃, 200 MHz) δ 7.3 (s, 1H), 7.0 (m, 10H), 4.1 (t, 2H), 4.0 (t, 2H), 3.8 (s, 3H), 3.1 (m, 4H), 3.0 (m, 2H), 2.7 (m, 4H), 2.6 (t, 2H), 1.8 (m, 4H)

Example 48

1-(2-methoxy-phenyl)-4-{4-[4-(2-[1,2,4]triazol-1-yl-ethyl)-phenoxy]-butyl}-piperazine

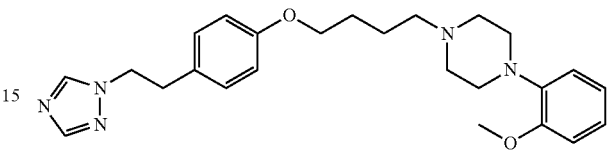

The procedure given in Example 47 was followed using 1H-1,2,4-triazole as a reactant, instead of imidazole, to give 1-(2-methoxy-phenyl)-4-{4-[4-(2-[1,2,4]triazol-1-yl-ethyl)-phenoxy]-butyl}-piperazine.

¹H-NMR (CDCl₃, 200 MHz) δ 8.0 (s, 1H), 7.8 (s, 1H), 7.0 (m, 8H), 4.4 (t, 2H), 4.0 (t, 2H), 3.8 (s, 3H), 3.1 (m, 6H), 2.7 (m, 4H), 2.5 (t, 2H), 1.8 (m, 4H)

Example 49

1-(2-methoxy-phenyl)-4-{4-[4-(2-[1,2,3]triazol-2-yl-ethyl)-phenoxy]-butyl}-piperazine

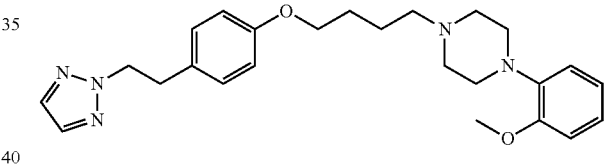

The procedure given in Example 47 was followed using 1H-1,2,3-triazole as a reactant, instead of imidazole, to give 1-(2-methoxy-phenyl)-4-{4-[4-(2-[1,2,3]triazol-2-yl-ethyl)-phenoxy]-butyl}-piperazine.

¹H-NMR (CDCl₃, 200 MHz) δ 7.7 (s, 2H), 7.0 (m, 8H), 4.6 (t, 2H), 4.0 (t, 2H), 3.8 (s, 3H), 3.1 (m, 6H), 2.7 (m, 4H), 2.5 (t, 2H), 1.8 (m, 4H)

Example 50

1-(2-methoxy-phenyl)-4-{4-[4-(2-[1,2,3]triazol-1-yl-ethyl)-phenoxy]-butyl}-piperazine

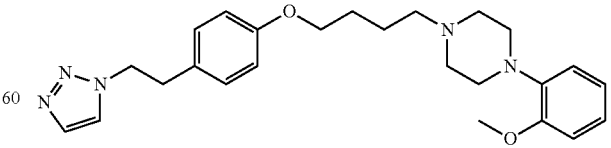

The procedure given in Example 47 was followed using 1H-1,2,3-triazole as a reactant, instead of imidazole, to give 1-(2-methoxy-phenyl)-4-{4-[4-(2-[1,2,3]triazol-1-yl-ethyl)-phenoxy]-butyl}-piperazine.

¹H-NMR (CDCl₃, 200 MHz) δ 7.6 (s, 1H), 7.3 (s, 1H), 7.0 (m, 8H), 4.6 (t, 2H), 4.0 (t, 2H), 3.8 (s, 3H), 3.1 (m, 6H), 2.7 (m, 4H), 2.5 (t, 2H), 1.8 (m, 4H)

Example 51

1-(2-methoxy-phenyl)-4-{4-[4-(2-tetrazol-2-yl-ethyl)-phenoxy]-butyl}-piperazine

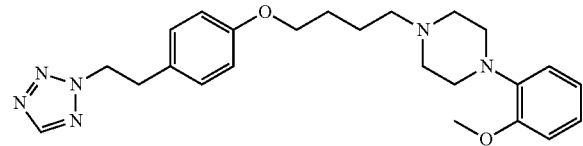 [SMILES: COc1ccccc1N1CCN(CCCCOc2ccc(CCn3ncnn3)cc2)CC1]

The procedure given in Example 47 was followed using 1H-tetrazole as a reactant, instead of imidazole, to give 1-(2-methoxy-phenyl)-4-{4-[4-(2-tetrazol-2-yl-ethyl)-phenoxy]-butyl}-piperazine.

¹H-NMR (CDCl₃, 200 MHz) δ 8.5 (s, 1H), 7.0 (m, 8H), 4.9 (t, 2H), 4.0 (t, 2H), 3.8 (s, 3H), 3.3 (t, 2H), 3.1 (m, 4H), 2.7 (m, 4H), 2.5 (t, 2H), 1.8 (m, 4H)

Example 52

1-(2-methoxy-phenyl)-4-{4-[4-(2-tetrazol-1-yl-ethyl)-phenoxy]-butyl}-piperazine

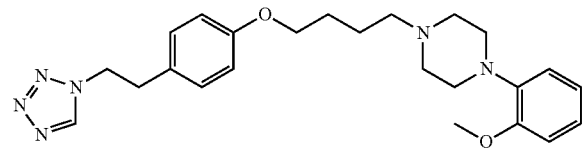 [SMILES: COc1ccccc1N1CCN(CCCCOc2ccc(CCn3cnnn3)cc2)CC1]

The procedure given in Example 47 was followed using 1H-tetrazole as a reactant, instead of imidazole, to give 1-(2-methoxy-phenyl)-4-{4-[4-(2-tetrazol-1-yl-ethyl)-phenoxy]-butyl}-piperazine.

¹H-NMR (CDCl₃, 200 MHz) δ 8.2 (s, 1H), 7.0 (m, 8H), 4.7 (t, 2H), 4.0 (t, 2H), 3.8 (s, 3H), 3.1 (m, 6H), 2.7 (m, 4H), 2.5 (t, 2H), 1.8 (m, 4H)

Example 53

1-(2-Methoxy-phenyl)-4-(4-{4-[2-(5-methyl-tetrazol-1-yl)-ethyl]-phenoxy}-butyl)-piperazine

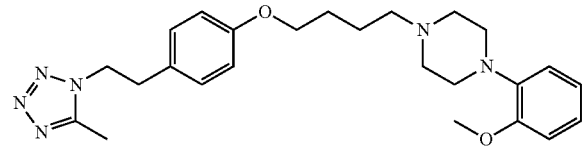 [SMILES: COc1ccccc1N1CCN(CCCCOc2ccc(CCn3nnnc3C)cc2)CC1]

The procedure given in Example 47 was followed using 5-Methyl-tetrazole as a reactant, instead of imidazole, to give 1-(2-Methoxy-phenyl)-4-(4-{4-[2-(5-methyl-tetrazol-1-yl)-ethyl]-phenoxy}-butyl)-piperazine.

¹H-NMR (CDCl₃, 200 MHz) δ 7.2~7.0 (m, 8H), 5.0 (t, 2H), 4.0 (t, 2H), 3.8 (s, 3H), 3.1 (m, 6H), 2.7 (m, 4H), 2.3~2.5 (m, 5H), 1.8 (m, 4H)

Example 54

1-(2-Methoxy-phenyl)-4-(4-{4-[2-(5-methyl-tetrazol-2-yl)-ethyl]-phenoxy}-butyl)-piperazine

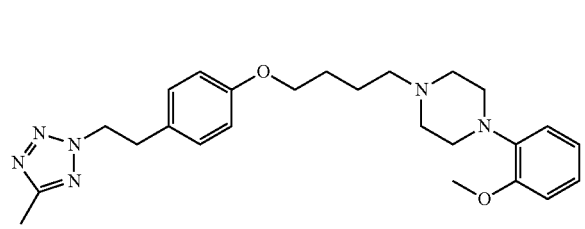 [SMILES: COc1ccccc1N1CCN(CCCCOc2ccc(CCn3nnc(C)n3)cc2)CC1]

The procedure given in Example 47 was followed using 5-Methyl-tetrazole as a reactant, instead of imidazole, to give 1-(2-Methoxy-phenyl)-4-(4-{4-[2-(5-methyl-tetrazol-2-yl)-ethyl]-phenoxy}-butyl)-piperazine.

¹H-NMR (CDCl₃, 200 MHz) δ 7.2~7.0 (m, 8H), 5.2 (t, 2H), 4.0 (t, 2H), 3.8 (s, 3H), 3.1 (m, 6H), 2.7 (m, 4H), 2.3~2.5 (m, 5H), 1.8 (m, 4H)

Example 55

2-{4-[4-(4-[1,2,3]-triazol-1-ylmethyl-phenoxy)-butyl]-piperazin-1-yl}-benzonitrile

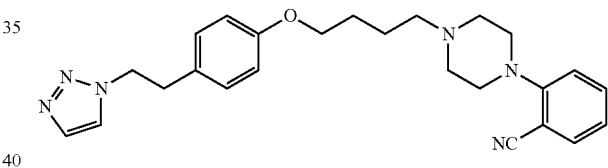

The procedure given in Example 1 was followed using 1-(2-cyano-phenyl)-piperazine and 1H-1,2,3-triazole as reactants, instead of 1-(2-methoxyphenyl)-piperazine and imidazole, to give 2-{4-[4-(4-[1,2,3]-triazol-1-ylmethyl-phenoxy)-butyl]-piperazin-1-yl}-benzonitrile.

¹H-NMR (CDCl₃, 200 MHz) δ 7.9 (s, 1H), 7.8 (s, 1H), 7.2 (m, 2H), 6.9 (m, 6H), 5.5 (s, 2H), 4.0 (t, 2H), 3.2 (m, 4H), 2.8 (m, 4H), 2.6 (t, 2H), 1.8 (m, 4H)

Example 56

1-(2-chloro-phenyl)-4-[4-(4-[1,2,3]triazol-2-ylmethyl-phenoxy)-butyl]-piperazine

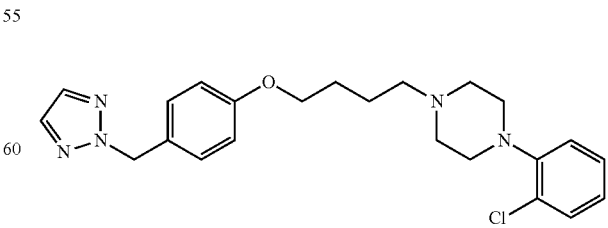

The procedure given in Example 1 was followed using 1-(2-chloro-phenyl)-piperazine and 1H-1,2,3-triazole as reactants, instead of 1-(2-methoxyphenyl)-piperazine and imidazole, to give 1-(2-chloro-phenyl)-4-[4-(4-[1,2,3]tria-zol-1-ylmethyl-phenoxy)-butyl]-piperazine.

$^1$H-NMR (CDCl$_3$, 200 MHz) δ 7.6 (s, 2H), 7.2 (m, 2H), 6.9 (m, 6H), 5.6 (s, 2H), 4.0 (t, 2H), 3.2 (m, 4H), 2.7 (m, 4H), 2.5 (t, 2H), 1.8 (m, 4H)

The therapeutic use of the compounds of general structural formula (I) and their pharmaceutically useful salts are demonstrated by the following tests.

Example 57

Serotonin 1A (5-HT1A) Receptor Inhibition Assay

The method to test the ability of compounds to inhibit serotonin 1A(5-HT1A) receptors was using Hall. et al., J Neuro Chem., 1985, 44, p 1685-1696 with modification.

The Sprague-Dawley (SD) rats were killed by decapitation and their brains rapidly removed at 4° C. The cortex tissue were homogenized in 30 volumes of ice-cold 50 mM Tris-HCl buffer (pH7.4) using an ultra-turrax T8 and centrifuged at 48,000 g for 20 min. The supernatant was discarded and the pellet washed twice by resuspension in 20 volumes Tris-HCl and centrifugation, homogenized in 20 volumes Tris-HCl, and incubated at 37° C. for 10 min. Membranes were than collected by centrifugation and washed twice before final resuspension in 10 volumes of 50 mM Tris-HCl, pH7.4.

For binding assays, the incubation medium consisted of 162.5 ug of tissue homogenate, 0.92 nM of [3H]8-OH-DPAT and vehicle or 10 uM of 5-HT or 10 nM of test compounds per well. 5-HT and test compounds were dissolved in distilled water and incubation medium was 50 mM Tris(pH7.4 at room temperature). The assay plates (96 well) were incubated for 60 min at 25° C. The reaction was terminated by rapid filtration using a Tomtec harvester, through GF/C glassfibre filter with 5 times washes of Tris buffer. The radioactivity retained on the filters was counted by scintillation spectroscopy (MicroBeta TriLux, Wallac). The tests were triplicates. Percent inhibition was calculated as below equation.

$$\% \text{ inhibition} = \frac{\text{Total binding} - \text{Compound binding}}{\text{Specific (Total} - \text{Nonspecific) binding}}$$

Total binding is the value of vehicle treated group and specific binding is the values that deduct non-specific binding (i.e. the value of non-specific ligand, 5-HT).

The results obtained by testing compounds of the invention are given in the following Table 1.

TABLE 1

| Test Compound | 5-HT1a % inhibition, at 10 nM |
|---|---|
| Example 1 | 83.1 |
| Example 2 | 80.3 |
| Example 3 | 77.8 |
| Example 4 | 75.9 |
| Example 5 | 50.7 |
| Example 6 | 50.1 |
| Example 7 | 78.4 |
| Example 8 | 81.6 |
| Example 9 | 52.2 |
| Example 10 | 71.8 |
| Example 11 | 61.8 |
| Example 12 | 60.9 |
| Example 13 | 50.4 |
| Example 14 | 51.1 |
| Example 15 | 23.5 |
| Example 16 | 62.5 |

TABLE 1-continued

| Test Compound | 5-HT1a % inhibition, at 10 nM |
|---|---|
| Example 17 | 56.4 |
| Example 18 | 69.5 |
| Example 19 | 59.6 |
| Example 20 | 68.5 |
| Example 21 | 38.2 |
| Example 22 | 53.4 |
| Example 23 | 17.2 |
| Example 24 | 51.6 |
| Example 25 | 45.2 |
| Example 26 | 47.0 |
| Example 27 | 40.9 |
| Example 28 | 13.5 |
| Example 29 | 45.8 |
| Example 30 | 38.3 |
| Example 31 | 30.3 |
| Example 33 | 53.7 |
| Example 35 | 73.3 |
| Example 36 | 28.1 |
| Example 37 | 24.8 |
| Example 38 | 29.4 |
| Example 39 | 52.9 |
| Example 40 | 45.6 |
| Example 41 | 82.1 |
| Example 42 | 36.2 |
| Example 43 | 95.6 |
| Example 44 | 17.4 |
| Example 45 | 73.8 |
| Example 46 | 64.6 |
| Example 47 | 70.0 |
| Example 48 | 48.0 |
| Example 49 | 45.0 |
| Example 50 | 51.0 |
| Example 51 | 47.0 |
| Example 52 | 62.0 |
| Example 53 | 46.0 |
| Example 54 | 71.0 |
| Example 56 | 24.3 |

Example 58

Tail Suspension Test in Mice (TST)

Tail Suspension Test in mice is the well-known animal model to determine antidepressant efficacy of compounds by checking escaping behavior and immobility time of mice. Mice treated with antidepressant drug show escaping behavior continuously comparing with control group.

The mice were mainly treated orally with the test compound dissolved in 30% PEG400 or with only 30% PEG400 as control. Tail of mouse is suspended to the rod of TST equipment and end of tail is fixed with sticky tape. Suspended mouse is incubated during 2 min for training and adaptation and after following 2 min, observe escaping behavior and check immobility time for 4 min. The potent ability of the compounds was determined as percent value of reduction in immobility comparing to control group as 100% baseline.

The results obtained by testing compounds of the invention are given in the following Table 2:

TABLE 2

| Test Compound | % reduction at 1 mg/kg, po |
|---|---|
| Example 5 | 21.2 |
| Example 7 | 21.1 |
| Example 8 | 19.6 |
| Example 11 | 25 |
| Example 12 | 12.7 |
| Example 18 | 14.7 |
| Example 19 | 50.6 |

TABLE 2-continued

| Test Compound | % reduction at 1 mg/kg, po |
|---|---|
| Example 33 | 26.8 |
| Example 39 | 30.4 |
| Example 40 | 10.6 |
| Example 41 | 14.1 |
| Example 48 | 26.2 |
| Example 49 | 34.3 |
| Example 50 | 46.9 |
| Example 51 | 14.7 |
| Example 52 | 26.4 |
| Example 54 | 31.8 |
| Estalopram | 47, at 30 mg/kg, po |
| Fluxetine | 49. at 30 mg/kg, po |

This anti-depressant effect, as with other anti-depressant drugs, suggested potentials for treating depression.

Example 59

Anti-Marble Burying Behavior Test in Mice

Marble burying was developed and validated as a pre-clinical assay of potential anxiolytic activity (Andrews and Broekkamp (1993). Procedures to Identify Anxiolytic or Anxiogenic agents. In Behavioural Neuroscience, ed. A Sahgal, pp. 37-54. IRL Press, Oxford). The marble burying test places a naive mouse into a novel environment containing 25 marbles (arranged on top of a sawdust surface). A reduction in the number of marbles buried by the mouse was hypothesized to be an anxiolytic-like effect.

The results obtained by testing compounds of the invention are given in the following Table 3:

TABLE 3

| Test Compound | % reduction, at 3 mg/kg, ip |
|---|---|
| Example 1 | 28.7 |
| Example 2 | 93.3 |
| Example 5 | 60.3, at 7.5 mg/kg, ip |
| Example 7 | 61.1, at 7.5 mg/kg, ip |
| Example 11 | 69.0, at 7.5 mg/kg, ip |
| Example 12 | 97.3 |
| Example 19 | 50.8, at 7.5 mg/kg, ip |
| Example 20 | 27.0, at 7.5 mg/kg, ip |
| Example 21 | 29.9 |
| Example 24 | 62.6 |
| Example 28 | 24.6 |
| Example 32 | 27.8, at 7.5 mg/kg, ip |
| Example 36 | 25.3 |
| Example 47 | 39.3 |
| Example 48 | 31.3 |
| Example 50 | 96.8, at 7.5 mg/kg, ip |
| Example 51 | 44.4, at 7.5 mg/kg, ip |
| Buspirone | 56.0, at 20 mg/kg, ip |

An anti-marble burying effect, as with other anti-anxiety drugs, suggested potentials for treating anxiety.

Example 60

Prophetic

A compound according to this invention is used to treat depression. A clinical dosage of 1 po (the basis of m-TST): 10 mg/human is used:

Example 61

Prophetic

A compound according to this invention is used to treat anxiety. A clinical dosage of 3 ip (m-MB): 30 mg/human is used.

Example 62

Prophetic

A capsule for the treatment of depression is prepared by conventional methods and formulated as follows:

Excipients: Avicel 102 (microcrystalline cellulose).

Capsule size: size "0"

TABLE 4

| Ingredient | Amount |
|---|---|
| Compound prepared in Example 48 | 10 mg |
| Microcrystalline cellulose | 240.7 mg |
| Sodium starch glycolate | 8 mg |
| Magnesium stearate | 1.3 mg |
| Total amount (net fill weight requirement) | 260 mg |

One or two capsules per day are administered to a human of 60 kg.

Example 63

Prophetic

A capsule for the treatment of anxiety is prepared by conventional methods and formulated as follows:

Excipients: Avicel 102 (microcrystalline cellulose).

Capsule size: size "0"

TABLE 5

| Ingredient | Amount |
|---|---|
| Compound prepared in Example 48 | 30 mg |
| Microcrystalline cellulose | 220.7 mg |
| Sodium starch glycolate | 8 mg |
| Magnesium stearate | 1.3 mg |
| Total amount (net fill weight requirement) | 260 mg |

One or two capsules per day are administered to a human of 60 kg.

What is claimed is:

1. A method for treating at least one of depression and anxiety in a mammal comprising administering to a mammal in need thereof an effective amount of a piperazine compound represented by Formula (I):

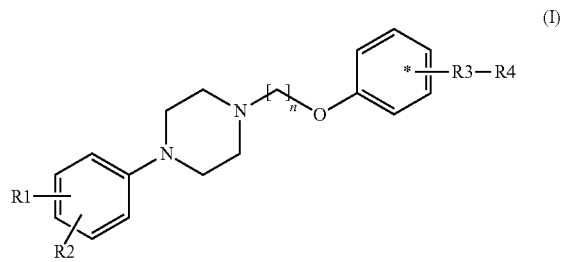

(I)

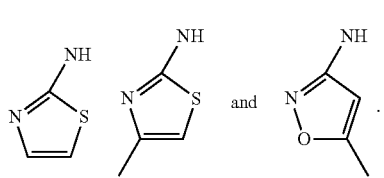

(II)

or pharmaceutically acceptable salts thereof,
wherein
n is an integer from 2 to 6;
R1 and R2 are the same or different and are independently selected from the group consisting of hydrogen, a hydroxyl group, a halogen, nitrogen dioxide, a straight or branched chain-alkyl group with 1 to 4 carbon atoms, and a straight or branched chain alkoxy group with 1 to 4 carbon atoms;
R3 is a C1-C2 alkylene; and
R4 is selected from the group consisting of:
(a) a C2-C6 dialkylamine,
(b) a 5 to 9-membered aromatic amine wherein the ring is independently substituted with at least one of hydrogen, a C1-C6 aliphatic alkyl, a C3 to C10 cyclic alkyl, a C6-C10 aryl group and a halogen,
(c) a 5 to 9-membered heteroaromatic amine comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen,
(d) a 5 to 9-membered heterocyclic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen, and
(e) a 5 to 9-membered heteroaromatic ring comprising at least a nitrogen atom as a ring constituent wherein the ring is independently substituted with at least one of hydrogen, a C1-C6 aliphatic alkyl, a C3 to C10 cyclic alkyl, a C6-C10 aryl group and a halogen; and
R4 is connected to R3 group through a nitrogen atom therein,
wherein R4 is not morpholine.

2. The method of claim 1, wherein R4 is dimethylamine or diethylamine.

3. The method of claim 1, wherein R4 is connected to R3 through a nitrogen atom in an amino group of the 5 to 9-membered aromatic amine or heteroaromatic amine.

4. The method of claim 3, wherein R4 is a 5 or 6-membered aromatic amine substituted with at least one of hydrogen, a C1-C6 alkyl, and a halogen.

5. The method of claim 4, wherein R4 is a 6-membered aromatic amine substituted with hydrogen.

6. The method of claim 3, wherein R4 is a 5 or 6-membered heteroaromatic amine substituted with at least one of a C1-C6 alkyl and a halogen, wherein the heteroaromatic amine comprises at least two heteroatoms as ring constituents where a first heteroatom is N and a second heteroatom is independently selected from the group consisting of N, O, and S.

7. The method of claim 6, wherein R4 is a 5-membered heteroaromatic amine having a structure (II) selected from the group consisting of:

8. The method of claim 1, wherein R4 is connected to R3 through a nitrogen atom contained in a ring as a heteroatom of the 5 to 9-membered heterocyclic ring or heteroaromatic ring.

9. The method of claim 8, wherein R4 is a 5 or 6-membered heterocyclic ring having a structure (III) selected from the group consisting of:

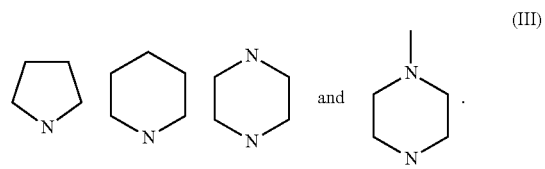

(III)

10. The method of claim 8, wherein R4 is an azole selected from the group consisting of diazole, triazole, tetraazol, benzotriazole, imidazole, pyrazole, benzimidazloe, and indazole.

11. The method of claim 10, wherein the azole has a structure (IV) selected from the group consisting of:

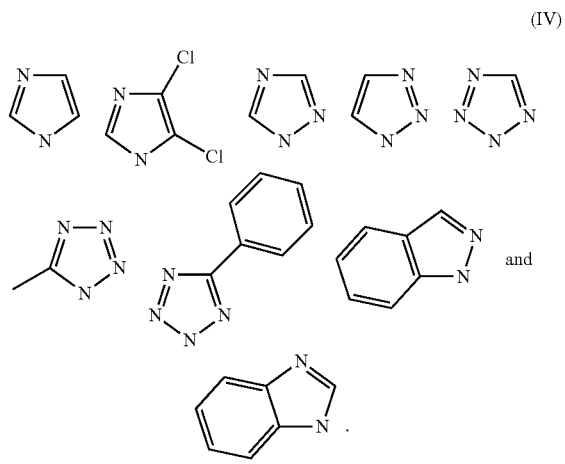

(IV)

12. The method of claim 1, wherein R1 and R2 are independently selected from the group consisting of hydrogen, a halogen, a straight or branched chain alkyl group with 1 to 4 carbon atoms, and a straight or branched chain alkoxy group with 1 to 4 carbon atoms.

13. The method of claim 1, wherein said compound is selected from the group consisting of:
1-[4-(4-imidazol-1-ylmethyl-phenoxy)-butyl]-4-(2-methoxy-phenyl)-piperazine, 1-(2-methoxy-phenyl)-4[4-(4-[1,2,4]triazol-1-ylmethyl-phenoxy)-butyl]-piperazine;
1-(2-methoxy-phenyl)-4-[4-(4-tetrazol-1-ylmethyl-phenoxy)-butyl]-piperazine;
1-(2-methoxy-phenyl)-4-[4-(4-tetrazol-2-ylmethyl-phenoxy)-butyl]-piperazine;
1-[4-(3-imidazol-1-ylmethyl-phenoxy)-butyl]-4-(2-methoxy-phenyl)-piperazine-hydrochloride;

1-(2-methoxy-phenyl)-4-[4-(3-[1,2,4]triazol-1-ylmethyl-phenoxy)-butyl]-piperazine hydrochloride;
1-(2-methoxy-phenyl)-4-[4-(3-tetrazol-1-ylmethyl-phenoxy)-butyl]-piperazine hydrochloride;
1-(2-methoxy-phenyl)-4-[4-(3-tetrazol-2-ylmethyl-phenoxy)-butyl]-piperazine hydrochloride;
1-(4-{4-[4-(2-methoxy-phenyl)-piperazin-1-yl]-butoxy}-benzyl)-1H-benzoimidazole;
1-(2-Methoxy-phenyl)-4-{4-[4-(2-methyl-imidazol-1-ylmethyl)-phenoxy]-butyl}-piperazine;
1-(2-methoxy-phenyl)-4-[4-(4-[1,2,3]triazol-2-ylmethyl-phenoxy)-butyl]-piperazine;
1-(2-methoxy-phenyl)-4-[4-(4-[1,2,3]triazol-1-ylmethyl-phenoxy)-butyl]-piperazine;
1-(4-{4-[4-(2-Methoxy-phenyl)-piperazin-1-yl]-butoxy}-benzyl)-1H-indazole;
1-(4-{4-[4-(2-Methoxy-phenyl)-piperazin-1-yl]-butoxy}-benzyl)-1H-benzotriazole;
1-(2-methoxy-phenyl)-4-{4-[4-(5-phenyl-tetrazol-2-ylmethyl)-phenoxy]-butyl}-piperazine;
1-(2-methoxy-phenyl)-4-{4-[4-(5-phenyl-tetrazol-1-ylmethyl)-phenoxy]-butyl}-piperazine;
1-(2-methoxy-phenyl)-4-{4-[4-(5-methyl-tetrazol-2-ylmethyl)-phenoxy]-butyl}-piperazine;
1-(2-methoxy-phenyl)-4-{4-[4-(5-methyl-tetrazol-1-ylmethyl)-phenoxy]-butyl}-piperazine;
(4-{4-[4-(2-methoxy-phenyl)-piperazin-1-yl]-butoxy}-benzyl)-dimethyl-amine di-hydrochloride;
1-(2-methoxy-phenyl)-4-[4-(4-piperidin-1-ylmethyl-phenoxy)-butyl]-piperazine;
(4-{4-[4-(2-methoxy-phenyl)-piperazin-1-yl]-butoxy}-benzyl)-phenyl-amine;
(4-{4-[4-(2-methoxy-phenyl)-piperazin-1-yl]-butoxy}-benzyl)-thiazol-2-yl-amine;
1-(2-chloro-phenyl)-4-[4-(4-[1,2,4]triazol-1-ylmethyl-phenoxy)-butyl]-piperazine;
1-(2-methoxy-phenyl)-4-[[4-(3-[1,2,3]triazol-2-ylmethyl-phenoxy)-butyl]-piperazine;
1-(2-Methoxy-phenyl)-4-[4-(3-[1,2,3]triazol-1-ylmethyl-phenoxy)-butyl]-piperazine;
1-(2-Methoxy-phenyl)-4-[4-(3-[1,2,3]triazol-2-ylmethyl-phenoxy)-butyl]-piperazine;
1-(2-methoxy-phenyl)-4-{4-[3-(5-methyl-tetrazol-1-ylmethyl)-phenoxy]-butyl}-piperazine;
(3-{4-[4-(2-methoxy-phenyl)-piperazin-1-yl]-butoxy}-benzyl)-dimethyl-amine;
1-{4-[4-(4,5-dichloro-imidazol-1-ylmethyl)-phenoxy]-butyl}-4-(2-methoxy-phenyl)-piperazine;
1-(2-chloro-phenyl)-4-[4-(4-tetrazol-2-ylmethyl-phenoxy)-butyl]-piperazine;
(4-{4-[4-(2-Chloro-phenyl)-piperazin-1-yl]-butoxy}-benzyl)-dimethyl-amine;
1-(3-fluoro-phenyl)-4-[4-(4-[1,2,4]triazol-1-ylmethyl-phenoxy)-butyl]-piperazine;
1-(2-methoxy-phenyl)-4-[4-(4-4-methylpiperazine-1-yl-methyl-phenoxy)-butyl]-piperazine;
1-(2,3-dichloro-phenyl)-4-[4-(4-tetrazol-2-ylmethyl-phenoxy)-butyl]-piperazine;
1-(2,3-Dichloro-phenyl)-4-{4-[4-(5-methyl-tetrazol-1-ylmethyl)-phenoxy]-butyl}-piperazine;
1-(2,3-Dichloro-phenyl)-4-{4-[4-(5-methyl-tetrazol-2-ylmethyl)-phenoxy]-butyl}-piperazine;
(4-{4-[4-(2,3-dichloro-phenyl)-piperazin-1-yl]-butoxy}-benzyl)-dimethyl-amine;
1-(2-methoxy-phenyl)-4-[4-(4-4-methylpiperazine-1-yl-methyl-phenoxy)-butyl]-piperazine;
1-(2-chloro-phenyl)-4-[4-(4-[1,2,3]triazol-1-ylmethyl-phenoxy)-butyl]-piperazine;
(4-{4-[4-(2-Methoxy-phenyl)-piperazin-1-yl]-butoxy}-benzyl)-[1,3,4]thiadiazol-2-yl-amine;
1-(2,3-dichloro-phenyl)-4-[4-(4-[1,2,3]triazol-1-ylmethyl-phenoxy)-butyl]-piperazine;
(4-{4-[4-(2-Methoxy-phenyl)-piperazin-1-yl]-butoxy}-benzyl)-(5-methyl-isoxazol-3-yl)-amine;
(4-{4-[4-(2-methoxy-phenyl)-piperazin-1-yl]-butoxy}-benzyl)-(5-methyl-isoxazol-3-yl)-amine;
1-{4-[4-(2-imidazol-1-yl-ethyl)-phenoxy]-butyl}-4-(2-methoxy-phenyl)-piperazine;
1-(2-methoxy-phenyl)-4-{4-[4-(2-[1,2,4]triazol-1-yl-ethyl)-phenoxy]-butyl}-piperazine;
1-(2-methoxy-phenyl)-4-{4-[4-(2-[1,2,3]triazol-2-yl-ethyl)-phenoxy]-butyl}-piperazine;
1-(2-methoxy-phenyl)-4-{4-[4-(2-[1,2,3]triazol-1-yl-ethyl)-phenoxy]-butyl}-piperazine;
1-(2-methoxy-phenyl)-4-{4-[4-(2-tetrazol-2-yl-ethyl)-phenoxy]-butyl}-piperazine;
1-(2-methoxy-phenyl)-4-{4-[4-(2-tetrazol-1-yl-ethyl)-phenoxy]-butyl}-piperazine;
1-(2-Methoxy-phenyl)-4-(4-{4-[2-(5-methyl-tetrazol-1-yl)-ethyl]-phenoxy}-butyl)-piperazine;
1-(2-Methoxy-phenyl)-4-(4-{4-[2-(5-methyl-tetrazol-2-yl)-ethyl]-phenoxy}-butyl)-piperazine;
2-{4-[4-(4-[1,2,3]-triazol-1-ylmethyl-phenoxy)-butyl]-piperazin-1-yl}-benzonitrile; and
1-(2-chloro-phenyl)-4-[4-(4-[1,2,3]triazol-2-ylmethyl-phenoxy)-butyl]-piperazine.

14. The method of claim 1, wherein the piperazine compound represented by Formula (I) is administered in a pharmaceutical composition, wherein the pharmaceutical composition further comprises a pharmaceutically acceptable carrier or excipient.

* * * * *